(12) United States Patent
Wang et al.

(10) Patent No.: US 12,127,857 B2
(45) Date of Patent: Oct. 29, 2024

(54) ASSISTED SCREENING OF DOWN SYNDROME SKIN PRINTS BASED ON MACHINE LEARNING ALGORITHM

(71) Applicant: SHANGHAI INSTITUTE OF NUTRITION AND HEALTH, CHINESE ACADEMY OF SCIENCES, Shanghai (CN)

(72) Inventors: Sijia Wang, Shanghai (CN); Jinxi Li, Shanghai (CN)

(73) Assignee: SHANGHAI INSTITUTE OF NUTRITION AND HEALTH, CHINESE ACADEMY OF SCIENCES, Shanghai (CN)

( * ) Notice: Subject to any disclaimer, the term of this patent is extended or adjusted under 35 U.S.C. 154(b) by 710 days.

(21) Appl. No.: 17/295,692

(22) PCT Filed: Nov. 20, 2019

(86) PCT No.: PCT/CN2019/119785
§ 371 (c)(1),
(2) Date: May 20, 2021

(87) PCT Pub. No.: WO2020/103881
PCT Pub. Date: May 28, 2020

(65) Prior Publication Data
US 2021/0386381 A1    Dec. 16, 2021

(30) Foreign Application Priority Data
Nov. 20, 2018   (CN) .......................... 201811384921.7

(51) Int. Cl.
*A61B 5/00*    (2006.01)
*A61B 5/1172*  (2016.01)
*A61B 5/1174*  (2016.01)

(52) U.S. Cl.
CPC .......... *A61B 5/7275* (2013.01); *A61B 5/0064* (2013.01); *A61B 5/1172* (2013.01);
(Continued)

(58) Field of Classification Search
CPC ... A61B 5/7275; A61B 5/0064; A61B 5/1172; A61B 5/1174; A61B 2503/04;
(Continued)

(56) References Cited

U.S. PATENT DOCUMENTS 7,406,186 B2    7/2008 Lin
9,292,916 B2 *  3/2016 Rowe ..................... G06V 40/70
(Continued)

FOREIGN PATENT DOCUMENTS

CN    1477587 A    2/2004
CN    1957360 A    5/2007
(Continued)

OTHER PUBLICATIONS

Wojtowicz et al., "The Design of Knowledge-Based Medical Diagnosis System for Recognition and Classification of Dermatoglyphic Features," *ACIIDS*, Part II, pp. 13-22, 2014.

*Primary Examiner* — Abhishek Sarma
(74) *Attorney, Agent, or Firm* — BANNER & WITCOFF, LTD.

(57) ABSTRACT

An assisted early screening system for Down syndrome, relating to assisted screening of Down syndrome skin prints based on a machine learning algorithm, wherein the system comprising: (a) a skin print feature input module; (b) a processing module for diagnosis of Down syndrome based on skin print, wherein the processing module performs a scoring processing on the inputted skin print features according to a predetermined evaluation criteria to obtain a risk score, and compares the risk score with a Down syndrome risk threshold, thereby obtaining an assisted
(Continued)

screening result; and (c) an output module for assisted screening result, which is configured to output the assisted screening result. The assisted early screening system for Down syndrome can implement simple, accurate, and effective assisted early screening of Down syndrome, such that powerful assistance can be provided for postnatal early intervention for early Down syndrome patients.

12 Claims, 5 Drawing Sheets

(52) U.S. Cl.
CPC ......... *A61B 5/1174* (2013.01); *A61B 2503/04* (2013.01); *A61B 2503/06* (2013.01)

(58) Field of Classification Search
CPC .. A61B 2503/06; A61B 5/7267; G06N 20/10; G06N 20/20; G16H 30/20; G16H 30/40; G16H 50/20; G16H 50/30; G16H 50/70
See application file for complete search history.

(56) References Cited

U.S. PATENT DOCUMENTS

| 2006/0165269 | A1 | 7/2006 | Lin |
| 2013/0202182 | A1 | 8/2013 | Rowe |

FOREIGN PATENT DOCUMENTS

| CN | 106716425 A | 5/2017 |
| WO | WO-2005/059805 A2 | 6/2005 |
| WO | WO-2013/023087 A1 | 2/2013 |
| WO | WO-2016/039950 A1 | 3/2016 |

* cited by examiner

ASSISTED SCREENING OF DOWN SYNDROME SKIN PRINTS BASED ON MACHINE LEARNING ALGORITHM

CROSS REFERENCE TO RELATED APPLICATIONS

This application is the National Stage of International Application No. PCT/CN2019/119785, filed Nov. 20, 2019, and claims benefit of Chinese Application No. 201811384921.7, filed on Nov. 20, 2018, the full contents of all of which are hereby incorporated by reference in their entirety.

TECHNICAL FIELD

The present invention relates to the field of medical diagnostics, and more particularly to assisted screening of Down syndrome skin prints based on machine learning algorithms.

BACKGROUND

Down syndrome is a hereditary disease. The number of patients with Down syndrome is huge and the birth rate is high. The birth rate is approximately 1/1000 (Weijerman and de Winter, 2011) in the world. There are about 23000-25,000 patients in China.

Currently, the early prenatal screening for Down syndrome is insufficient. There are a variety of prenatal screening methods, especially new technologies in which fetal free DNA is used for sequencing to detect whether there is chromosomal variation. However, because of the complexity of experiments and data analysis, dependence on a professional team, and relatively high test cost, it is difficult to carry out large-scale promotion in various regions, especially in rural areas with poor economic conditions in China (Kazemi, et al., 2016). Therefore, there is still a lack of early prenatal screening methods for Down patients.

Studies have shown that early intervention for Down patients is very important. Early intervention can effectively improve the social, emotional and cognitive ability of patients with Down syndrome, and most patients can achieve their own self-care, take public transportation, and participate in public welfare activities (Hanson, 2003).

At present, there is insufficient early screening for Down syndrome patients after birth. The realization of early intervention is based on whether the post-birth patients can be screened early. Although features such as special face, behavior, and mental retardation can provide important clues, they can neither reflect "early", nor calculate their accuracy.

Therefore, it is an urgent need in the art to develop a more efficient, earlier and more accurate method and an apparatus for assisted screening of Down syndrome.

SUMMARY OF INVENTION

It is an object of the present invention to provide a more efficient, earlier and more accurate method and an apparatus for assisted screening of Down syndrome.

In the first aspect of the invention, it provides an early assisted screening system for Down syndrome, which comprises:

(a) a skin print feature input module, which is configured to input skin print features of a subject;

wherein the skin print features comprise two features selected from the following Group A: V7—pattern on the ball of right foot, and V33—left hand atd angle;

(b) a processing module for diagnosis of Down syndrome based on skin print, wherein the processing module performs a scoring processing on the inputted skin print features according to a predetermined evaluation criteria to obtain a risk score, and compares the risk score with a Down syndrome risk threshold, thereby obtaining an assisted screening result; wherein, when the risk score is higher than the risk threshold, it indicates that the subject's risk of Down syndrome is higher than that of a normal population; and when the risk score is lower than the risk threshold, it indicates that the subject's risk of Down syndrome is lower than that of the normal population; and (c) an output module for assisted screening result, which is configured to output the assisted screening result.

In another preferred embodiment, the skin print features further comprise 1, 2, 3 or 4 features selected from the following Group B:

V56—right hand D5R inter-finger fold(s);
V19—number of left-hand D4L crest line(s);
V29—left-hand print in IV zone; and
V23—whether left hand has an simian crease.

In another preferred embodiment, the skin print features comprise two skin print features from Group A and 3 or 4 skin print features from Group B.

In another preferred embodiment, the skin print features comprise: V7-pattern on the ball of right foot; V33-left hand atd angle; V56-D5R inter-finger fold; V19-D4L number of crest line; V29-left hand print in IV zone; and V23—whether the left hand has an simian crease.

In another preferred embodiment, the skin print features further comprise at least 2 features selected from Group C1:
V1, V54, V56, V19, V16, V35, and V29.

In another preferred embodiment, the skin print features further comprise at least one feature selected from Group C2:
V55, V50, V28, V42, V44, and V43.

In another preferred embodiment, the skin print features further comprise at least one feature selected from Group D:
V50, V28, V35, and V53.

In another preferred embodiment, the skin print features comprise two skin print features of Group A and 4 skin print features of Group B and optionally 1-4 skin print features from Group D.

In another preferred embodiment, the subject is a human being.

In another preferred embodiment, the subject comprises an infant, a young people or an adult.

In another preferred embodiment, the subject is 1 month to 44 years old, preferably 2 months to 10 years old, and more preferably 2 months to 5 years old.

In another preferred embodiment, the skin print features are scored as defined in Table A, especially according to the manner of the penultimate column in Table A.

In another preferred embodiment, in the processing module, risk score processing is performed as follows:

V7—pattern on the ball of right foot: when the arch print is present, the risk of disease is increased (more than 90% of the arch print appears in the disease group, while only about 10% of the arch print appears in the control group, $P=1.35\times10^{-139}$);

V33-left hand atd angle: when the angle is greater than 50 degrees, the risk of disease increases (the average angle in the disease group is more than 60 degrees, while it is about 40 degrees in the control group, $P=2.46\times10^{-48}$);

V56-D5R inter-finger fold: when there is only one inter-finger fold or the little finger is bent, the risk of disease increases (V56 right-hand D5 inter-finger fold in the disease group mostly appears as only one inter-finger fold (30%-56%) or the little finger is bent), and while there is no single fold in the control group, $P=7.83\times10^{-99}$);

V19-D4L number of crest line: when the number of crest line is lower than an average of 11, the risk of disease increases (The number is 11 in the disease group and 16 in the control group, $P=3.86\times10^{-36}$);

V29—Left hand print in IV zone: when the left-hand print in IV zone appears as a bow-shaped non-real print in the disease group, the risk of disease increases (the incidence of real print (non-arch print) in the disease group is lower than 40%, and is about 80% in the control group, $P=8.02\times10^{-45}$);

V23—Whether left hand has an simian crease: when the left hand has simian crease print, the risk of disease increases (the incidence of simian crease is as high as 60% in the disease group, while it is only about 10% in the control group, $P=5.46\times10^{-46}$).

In another preferred embodiment, the score includes (a) a score of a single skin print feature; and/or (b) a sum of a plurality of skin print feature scores.

In another preferred embodiment, the skin print feature input module is selected from the group consisting of: a skin print collector, a scanner, a keyboard, a tablet computer (PAD), and a smart phone.

In another preferred embodiment, the processing module for diagnosis of Down syndrome based on skin print comprises a processor, and a memory in which the data of risk threshold of Down syndrome based on skin print feature are stored.

In another preferred embodiment, the output module comprises a display, a printer, a tablet computer (PAD), or a smart phone.

In another preferred embodiment, the modules are connected by wire or wireless.

In a second aspect of the present invention, it provides a method for early assisted screening of Down syndrome, which comprises:

(a) providing skin print features from a certain subject; the skin print features comprise two features selected from the following Group A: V7—pattern on the ball of right foot, and V33—left hand atd angle;

(b) performing a diagnosis of Down syndrome based on skin print, wherein the performing comprises: implementing a scoring processing on the inputted skin print features according to a predetermined evaluation criteria to obtain a risk score, and comparing the risk score with a Down syndrome risk threshold, thereby obtaining an assisted screening result; wherein, when the risk score is higher than the risk threshold, it indicates that the subject's risk of Down syndrome is higher than that of a normal population; and when the risk score is lower than the risk threshold, it indicates that the subject's risk of Down syndrome is lower than that of the normal population.

In another preferred embodiment, the skin print features comprise: V7-pattern on the ball of right foot; V33-left hand atd angle; V56-D5R inter-finger fold; V19-D4L number of crest line; V29-left hand print in IV zone; and V23—whether left hand has an simian crease.

It should be understood that, within the scope of the present invention, the above technical features of the present invention and the technical features specifically described hereinafter (e.g., in the examples) can be combined with each other, thereby forming a new or preferred technical solution, which is not redundantly described one-by-one due to space limitation.

BRIEF DESCRIPTION OF THE DRAWINGS

FIG. 2 shows in an example of the present invention, the importance ranking of the variables was obtained by XgBoost training on the skin print features, wherein FIG. 2a shows 29 skin print features (only the top 20 items are indicated); FIG. 2b shows 22 skin prints features (only the top 15 items indicated) after excluding features with high correlation.

FIG. 3 shows the performance of the number of features and training set and independent test set under XGBoost training, wherein FIG. 3a shows a false negative (FN) rate R; FIG. 3b shows an accuracy.

FIG. 6 shows the performance of the number of features and training set and independent test set under XGBoost training by using only finger and palm print features, wherein FIG. 6a shows a false negative rate (FNR); and FIG. 6b shows an accuracy.

DETAILED DESCRIPTION

Figure 1:
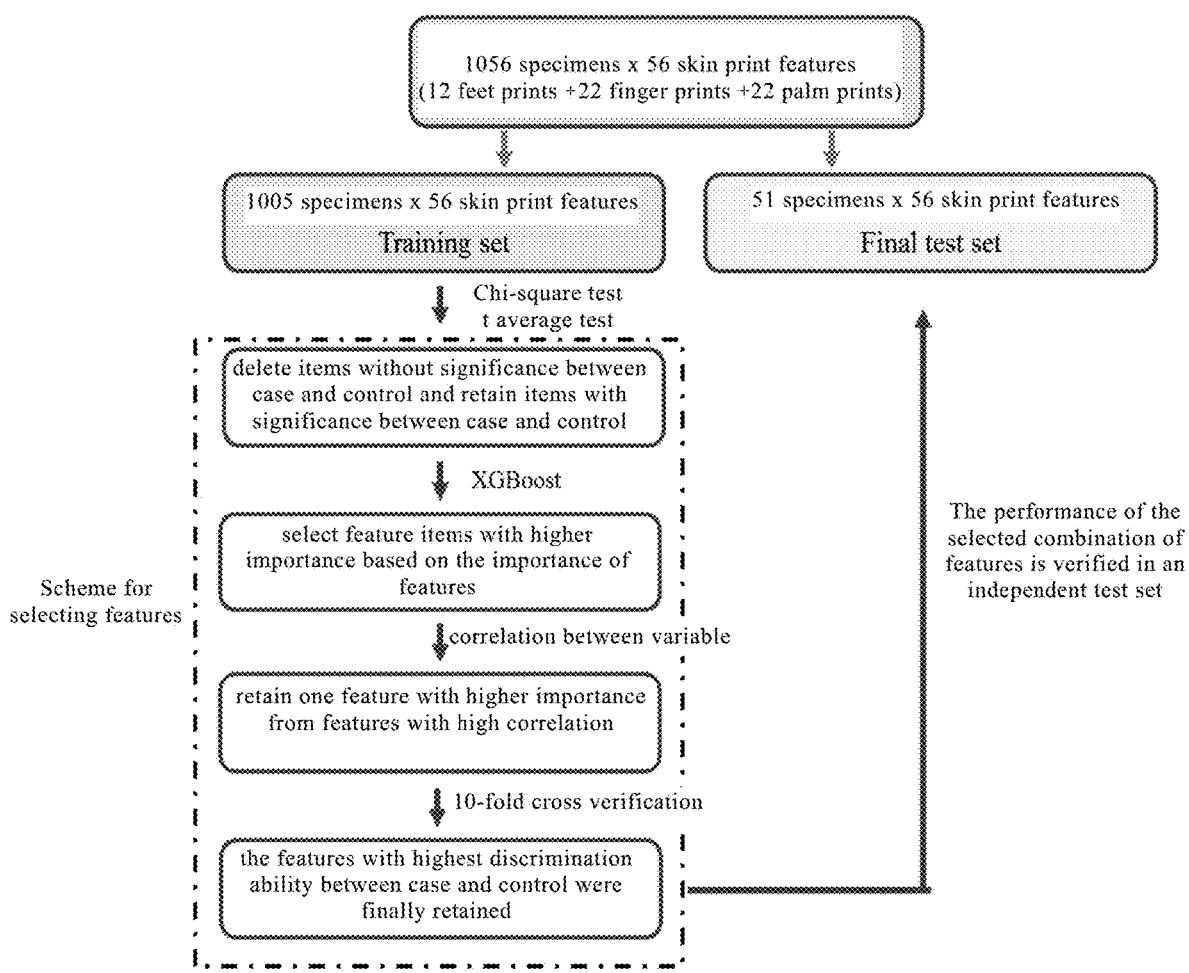
FIG. 1 shows a scheme for feature selection in the present invention.

After intensive and extensive researches, the present inventors have developed for the first time an effective and accurate method and device for early assisted screening of Down syndrome based on specific characteristic skin prints. Specifically, through in-depth research on the skin prints of a large number of population, the present inventors have unexpectedly screened out many characteristic features (or variables) closely related to Down syndrome from those easily observed characteristic skin prints formed after birth, thus constructing a simple, accurate and efficient early screening system for Down syndrome. The method and screening system of the present invention have many features such as non-invasive, high accuracy, low false negative rate, and easy promotion. On this basis, the present invention has been completed.

Terms

As used herein, the terms "characteristic skin print of the present invention" and "characteristic skin print related to Down syndrome of the present invention" are used interchangeably and refer to the skin prints in infants that are closely related to Down syndrome.

As used herein, the term "skin print" includes finger print, palm print, foot print, or combinations thereof.

As used herein, the term "skin print feature" refers to a feature for any type of skin print selected from finger print, palm print, and foot print. Skin print features can be obtained by conventional methods, including visual and instrumental measurements. Preferably, the skin print features of the present invention are as defined in Table A.

As used herein, the term "screening" includes detection for diagnostic or non-diagnostic purposes. The term includes early screening (or early diagnosis), as well as late screening or assisted screening (or assisted diagnosis); it includes both screening of a group and screening of an individual.

TABLE A

Description and Definition of 56 skin print features

| No. | Position | Phenotype Features | Feature Property | Feature Classification |
|---|---|---|---|---|
| V1 | Sole_L | pattern on ball of foot | 1-3 | 1-arch print (tibial tented arch (TAt), distal arch(Ad), tibial Arch(At), proximal arch(Ap), fibular arch (Af)); 2-loop print (distal loop(Ld), tibial loop(Lt), proximal loop(Lp), fibular loop(Lf)); 3-whorl print (W), 11-complex (C) |
| V2 | Sole_L | print in II zone | 1-2 | 1-non-real print - arch print, 2-other real print (distal loop (Ld), proximal loop(Lp), whorl (W)) |
| V3 | Sole_L | print in III zone | 1-2 | 1-non-real print - arch print, 2-other real print (distal loop, Ld), proximal loop(Lp), whorl (W), II/III zone distal loop real print) |
| V4 | Sole_L | print in IV zone | 1-2 | 1-non-real print-arch print, 2-other real print |
| V5 | Sole_L | hypothenar print | 1-2 | 1-non-real print - arch print, 2-other real print (tibial loop(Lt), whorl (W), fibular loop (Lf)) |
| V6 | Sole_L | sole print | 1-2 | 1-non-real print - arch print, 2-other real print (tibial loop (Lt), fibular loop(Lf)) |
| V7 | Sole_R | pattern on ball of foot | 1-3 | 1-arch print (tibial tented arch (TAt), distal arch(Ad), tibial Arch(At), proximal arch(Ap), fibular arch (Af)); 2-loop print (distal loop (Ld), tibial loop (Lt), proximal loop (Lp), fibular loop(Lf)), 3-whorl print (W), 11-complex whorl (C) |
| V8 | Sole_R | print in II zone | 1-2 | 1-non-real print - arch print, 2-other real print (distal loop (Ld), proximal loop(Lp), whorl (W)) |
| V9 | Sole_R | print in III zone | 1-2 | 1-non-real print - arch print, 2-other real print (distal loop (Ld), proximal loop(Lp), whorl (W), II/III zone distal loop real print) |
| V10 | Sole_R | print in IV zone | 1-2 | 1-non-real print-arch print, 2-other real print |
| V11 | Sole_R | hypothenar print | 1-2 | 1-non-real print - arch print, 2-other real print (tibial loop (Lt), whorl (W), fibular loop(Lf)) |
| V12 | Sole_R | sole print | 1-2 | 1-non-real print - arch print, 2-other real print (tibial loop (Lt), fibular loop(Lf)) |
| V13 | Finger_L | D5 finger print | 1-3 | 1-arch print (simple arch (As), tented arch(At)), 2-loop print (ruler loop (Lu), radial loop (Lr)), 3-whorl print (normal whorl (Ws), double-whorl (Wd)) |
| V14 | Finger_L | D4 finger print | 1-3 | 1-arch print (simple arch (As), tented arch(At)), 2-loop print (ruler loop (Lu), radial loop (Lr)), 3-whorl print (normal whorl (Ws), double- whorl, Wd)) |
| V15 | Finger_L | D3 finger print | 1-3 | 1-arch print (simple arch (As), tented arch(At)), 2-loop print (ruler loop (Lu), radial loop (Lr)), 3-whorl print (normal whorl (Ws), double- whorl, Wd)) |
| V16 | Finger_L | D2 finger print | 1-3 | 1-arch print (simple arch (As), tented arch(At)), 2-loop print (ruler loop (Lu), radial loop (Lr)), 3-whorl print (normal whorl (Ws), double- whorl, Wd)) |
| V17 | Finger_L | D1 finger print | 1-3 | 1-arch print (simple arch (As), tented arch(At)), 2-loop print (ruler loop (Lu), radial loop (Lr)), 3-whorl print (normal whorl (Ws), double- whorl, Wd)) |
| V18 | Finger_L | D5 finger crest line count | count | The arch print FRC is counted as 0; if it is a whorl print, choose bigger one from left side and right side. |
| V19 | Finger_L | D4 finger crest line count | count | The arch print FRC is counted as 0; if it is a whorl print, choose bigger one from left side and right side. |
| V20 | Finger_L | D3 finger crest line count | count | The arch print FRC is counted as 0; if it is a whorl print, choose bigger one from left side and right side. |
| V21 | Finger_L | D2 finger crest line count | count | The arch print FRC is counted as 0; if it is a whorl print, choose bigger one from left side and right side. |
| V22 | Finger_L | D1 finger crest line count | count | The arch print FRC is counted as 0; if it is a whorl print, choose bigger one from left side and right side. |
| V23 | Palm_L | whether it is simian crease | 1-2 | 1-non-simian crease hand, 2- simian crease hand |

TABLE A-continued

Description and Definition of 56 skin print features

| No. | Position | Phenotype Features | Feature Property | Feature Classification |
|---|---|---|---|---|
| V24 | Palm_L | Whether it has c, d, t | 1-5 | 1- has c\d\t, 3-lack of c area, 4-lack of d area, 5-lack of t area |
| V25 | Palm_L | a-b crest line count | count | ridge count between point a and point b |
| V26 | Palm_L | thenar print | 1-2 | 1-non-real print - arch print, 2-other real print (distal loop, radial loop, proximal loop, ruler loop, whorl, complex whorl, 8-degradation print; 1 = 8) |
| V27 | Palm_L | print in II zone | 1-2 | 1- non-real print, 2- real print |
| V28 | Palm_L | print in III zone | 1-2 | 1- non-real print, 2- real print |
| V29 | Palm_L | print in IV zone | 1-2 | 1- non-real print, 2- real print |
| V30 | Palm_L | II/III zone print | 1-2 | 1- non-real print, 2- real print |
| V31 | Palm_L | III/IV zone print | 1-2 | 1- non-real print, 2- real print |
| V32 | Palm_L | hypothenar print | 1-2 | 1-non-real print (arch print, degradation print), 2-other real prints (distal loop, ruler loop, proximal loop, radial loop, whorl, complex whorl, 8- degradation print; 1 = 8) |
| V33 | Palm_L | atd angle | count | angle value |
| V34 | Finger_R | D1 finger print | 1-3 | 1-arch print (simple arch (As), tented arch(At)), 2-loop print (ruler loop (Lu), radial loop (Lr)), 3-whorl print (normal whorl (Ws), double- whorl, Wd)) |
| V35 | Finger_R | D2 finger print | 1-3 | 1-arch print (simple arch (As), tented arch(At)), 2-loop print (ruler loop (Lu), radial loop (Lr)), 3-whorl print (normal whorl (Ws), double- whorl, Wd)) |
| V36 | Finger_R | D3 finger print | 1-3 | 1-arch print (simple arch (As), tented arch(At)), 2-loop print (ruler loop (Lu), radial loop (Lr)), 3-whorl print (normal whorl (Ws), double- whorl, Wd)) |
| V37 | Finger_R | D4 finger print | 1-3 | 1-arch print (simple arch (As), tented arch(At)), 2-loop print (ruler loop (Lu), radial loop (Lr)), 3-whorl print (normal whorl (Ws), double- whorl, Wd)) |
| V38 | Finger_R | D5 finger print | 1-3 | 1-arch print (simple arch (As), tented arch(At)), 2-loop print (ruler loop (Lu), radial loop (Lr)), 3-whorl print (normal whorl (Ws), double- whorl, Wd)) |
| V39 | Finger_R | D1 finger crest line count | count | The arch print FRC is counted as 0; if it is a whorl print, choose bigger one from left side and right side. |
| V40 | Finger_R | D2 finger crest line count | count | The arch print FRC is counted as 0; if it is a whorl print, choose bigger one from left side and right side. |
| V41 | Finger_R | D3 finger crest line count | count | The arch print FRC is counted as 0; if it is a whorl print, choose bigger one from left side and right side. |
| V42 | Finger_R | D4 finger crest line count | count | The arch print FRC is counted as 0; if it is a whorl print, choose bigger one from left side and right side. |
| V43 | Finger_R | D5 finger crest line count | count | The arch print FRC is counted as 0; if it is a whorl print, choose bigger one from left side and right side. |
| V44 | Palm_R | whether it is simian crease | 1-2 | 1-non-simian crease hand, 2- simian crease hand |
| V45 | Palm_R | Whether it has c, d, t | 1-5 | 1- has c\d\t, 3-lack of c area, 4-lack of d area, 5-lack of t area |
| V46 | Palm_R | a-b crest line count | count | ridge count between point a and point b |
| V47 | Palm_R | thenar print | 1-2 | 1-non-real print - arch print, 2-other real print (distal loop, radial loop, proximal loop, ruler loop, whorl, complex whorl, 8-degradation print; 1 = 8) |
| V48 | Palm_R | print in II zone | 1-2 | 1- non-real print, 2- real print |
| V49 | Palm_R | print in III zone | 1-2 | 1- non-real print, 2- real print |
| V50 | Palm_R | print in IV zone | 1-2 | 1- non-real print, 2- real print |
| V51 | Palm_R | II/III zone print | 1-2 | 1- non-real print, 2- real print |
| V52 | Palm_R | III/IV zone print | 1-2 | 1- non-real print, 2- real print |
| V53 | Palm_R | hypothenar print | 1-2 | 1-non-real print (arch print, degradation print), 2-other real prints (distal loop, ruler loop, proximal loop, radial loop, whorl, complex whorl, 8- degradation print; 1 = 8) |
| V54 | Palm_R | atd angle | count | angle value |
| V55 | Finger_L | D5 inter-finger fold | 1-3 | 1- 2 inter-finger normal folds, 2- 2 inter-finger folds with a bent little finger, 3- one inter-finger fold - exist in patients |

TABLE A-continued

Description and Definition of 56 skin print features

| No. | Position | Phenotype Features | Feature Property | Feature Classification |
|---|---|---|---|---|
| V56 | Finger_R | D5 fingertips | 1-3 | 1- 2 inter-finger normal folds, 2- 2 inter-finger folds with a bent little finger, 3- one inter-finger fold - exist in patients |

Skin Print and its Collection

Skin prints (including finger prints, palm prints and foot prints) begin to form during the 3 to 4 months of pregnancy and are rarely affected by the external environment after birth (Holder et al., 2011). Skin prints provide the possibility for early screening of patients with Down syndrome after birth.

In the present invention, skin print can be obtained by visual observation or instrumental measurement. For example, it can be performed with reference to Table A.

For a skin print profile, the skin print profile may be collected from the skin sites including fingers, palms, toes, and soles. Suitable methods for acquiring such print profile include: optical image capture based on the phenomenon of total internal reflection ("TIR"), direct optical imaging, capacitive radio frequency ("RF") and other semiconductor array capture devices, ultrasound, pressure arrays, etc.

In addition, optical capture can be performed in such a manner that a plurality of optical conditions are measured at the same skin site, thereby obtaining a skin print image and determining the characteristics of the skin prints.

In the present invention, suitable optical systems that can be used to collect skin prints may include multi-spectral and/or hyper-spectral capture devices that use one or more illumination wavelengths for illumination. The optical system can measure under one, two or more polarization conditions.

Characteristics of Skin Prints Related to Down Syndrome

Down syndrome can be screened early, based on the characteristic skin prints of the present invention. In the present invention, the selection of skin print features is performed according to the importance (Gain value) of each feature when constructing the model and the correlation between the features.

Figure 6:
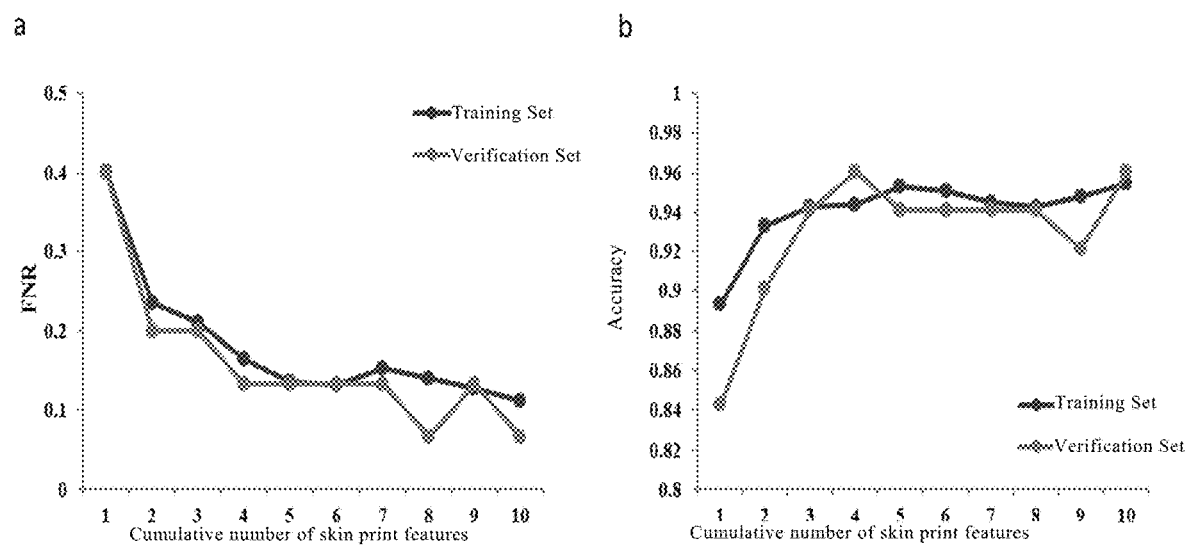

V7—pattern on the ball of right foot;
V33—left hand atd angle;
V56—D5R inter-finger fold;
V19—D4L number of crest lines;
V29—left-hand print in IV zone;
V23—left hand has an simian crease;
V50—right-hand print in IV zone
V28—left hand print in III zone
V35—D2R finger print
V53—Right hand hypothenar print In a preferred embodiment, only the top 6 skin print features are required, because when the first 6 skin print features are used for model construction, the results of FNR and accuracy have converged, and when the other features are further added, the top 7, top 8, top 9, and top 10 features showed little improvement (FIG. 6). In view of the construction of the skin print screening system, it is advisable to use the least feature items. Therefore, it is preferred to select the top 6 features or feature items as follows:

V7—pattern on the ball of right foot;
V33—left hand atd angle;
V56—D5R inter-finger fold;
V19—D4L number of crest lines;
V29—left-hand print in IV zone;
V23—left hand has an simian crease;

Certainly, in the present invention, one or more other skin print features listed in Table A can be further added, especially those skin print features ranking in the front.

Figure 7:
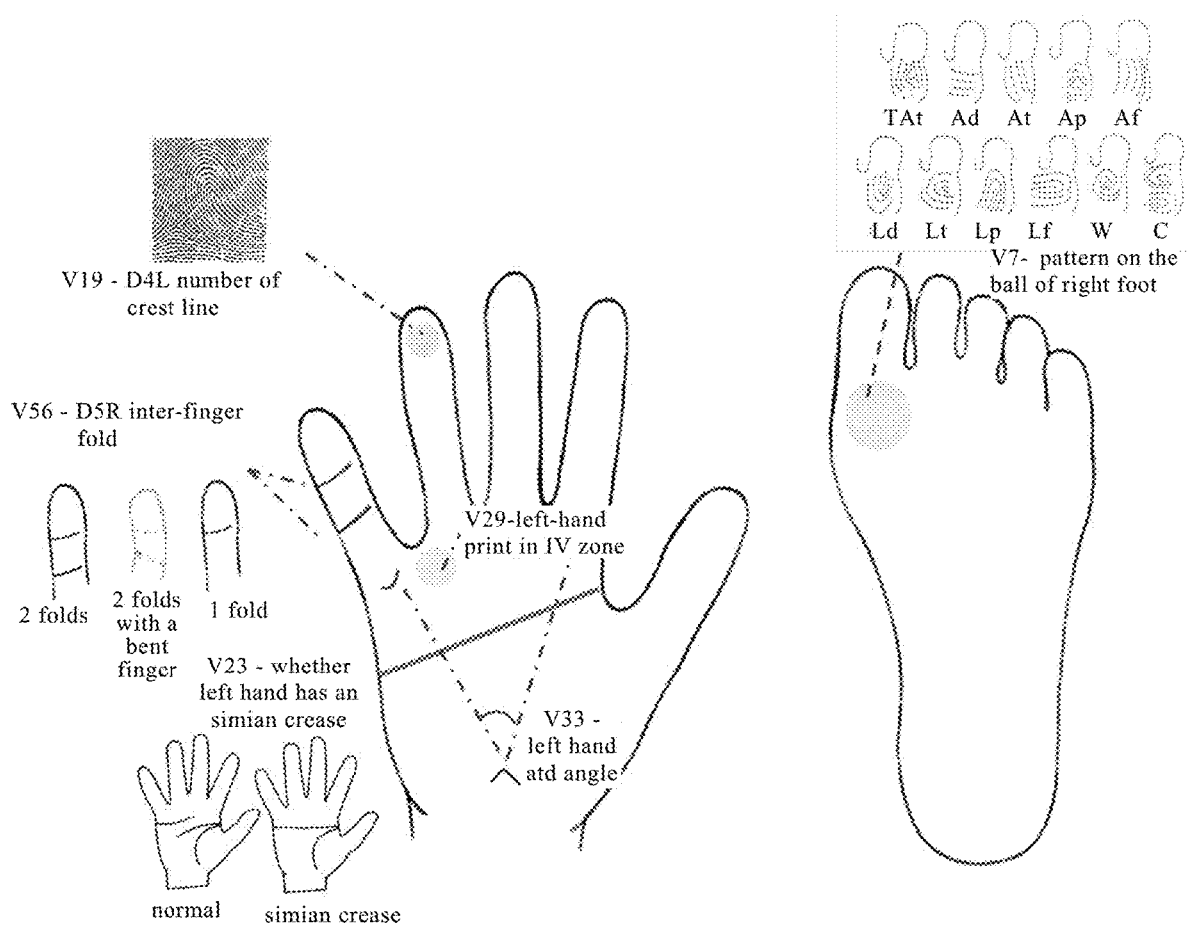
FIG. 7 shows a schematic view showing 6 preferred skin print features of Down syndrome in the skin print screening system of the present invention.

As shown in FIG. 7, for the top 6 skin print features, the research of the present invention shows that their specific differences between the disease group and the control group are as follows:

1) V7: pattern on the ball of right foot shows more than 90% arch print in the disease group, while the control group only has about 10% arch print ($P=1.35\times10^{-139}$);
2) V33: The angle of the left hand atd angle is significantly higher in the disease group than in the control group (61 in the disease group and 40 in the control group, $P=2.46\times10^{-48}$);
3) V56: The right hand D5 inter-finger fold is mostly manifested in the disease group as only one inter-finger fold (30%-56%) or the little finger is bent, but there is no single inter-finger fold in the control group;
4) V19: The number of left-hand D4 crest line in disease groups was significantly lower than that in the control group, that is, the number of finger print in the disease group was smaller (11 in the disease group and 16 in the control group, $P=3.86\times10^{-36}$);
5) V29: The occurrence rate of the real print (non-arch print) in the left-hand IV inter-finger print is less than 40% in the disease group, while is about 80% in the control group ($P=8.02\times10^{-45}$);
6) V23: The occurrence rate of left-handed simian crease is as high as 60% in the disease group, and is only about 10% in the control group ($P=5.46\times10^{-46}$).

Assisted Screening Method and Equipment for Down Syndrome

The present invention also provides a corresponding method and device for early assisted screening of Down syndrome, based on the characteristic skin prints provided by the present invention.

A typical early assisted screening system for Down syndrome is as described in the first aspect of the present invention. The system comprises:

(a) a skin print feature input module, which is configured to input skin print features of a subject; wherein the skin print features comprise two types selected from the following Group A: V7—pattern on the ball of right foot, and V33—left hand atd angle;

(b) a processing module for diagnosis of Down syndrome based on skin print, wherein the processing module performs a scoring processing on the inputted skin print features according to a predetermined evaluation criteria to obtain a risk score, and compares the risk score with a Down syndrome risk threshold, thereby obtaining an assisted screening result; wherein, when the risk score is higher than the risk threshold, it indicates that the subject's risk of Down syndrome is higher than that of a normal population; and when the risk score is lower than the risk threshold, it indicates that the subject's risk of Down syndrome is higher than that of the normal population; and (c) an output module for assisted screening result, which is configured to output the assisted screening result.

In the present invention, a manual input method or an automatic collection method may be used to input skin print features. Typically, the skin print feature input module is selected from the group consisting of a skin print collector, a scanner, a keyboard, a tablet computer (PAD), a smart phone, and combinations thereof.

Preferably, in the present invention, the processing module for diagnosis of Down syndrome based on skin print comprises a processor, and a memory in which the data of risk threshold of Down syndrome based on skin print feature are stored.

In the present invention, the representative output module comprises (but is not limited to): a display, a printer, a tablet computer (PAD), or a smart phone.

The early assisted screening system for Down syndrome of the present invention may be in the form of an integrated machine or discrete machines. For example, the skin print feature input module can be independent, and the collected or input skin print feature data can be transmitted to the local processing module by wired or wireless means, or can be uploaded to the non-local processing module (for example, remote center server) by WiFi or tele-communication to achieve remote screening.

In one embodiment, after the remote processing module evaluates the skin print features, the assisted screening result can be wirelessly transmitted to the output device which is connected to the network, such as a tablet computer (PAD) or a smartphone, in order to achieve rapid assisted screening.

In a preferred example of the present invention, when a device such as a skin print collection device is used and the image is uploaded through the input terminal, and it is essentially or basically not necessary to rely on manual reading of features, thereby greatly liberating manpower and highly reducing or even eliminating the requirement for medical staff to master the knowledge of skin prints, and is also helpful to improve the accuracy of screening.

The main advantages of the present invention include:

(a) For the first time, it provides an early aided screening method for Down syndrome with high accuracy and a very low false negative rate.

(b) The method of the present invention is not only simple but also non-invasive.

(c) The early assisted screening system or device for Down syndrome of the present invention can not only be popularized and applied in clinic, but also facilitate the implementation of remote intelligent assisted screening.

(d) The early assisted screening system or device for Down syndrome of the present invention uploads images through the input terminal without relying on manual reading of features, thereby greatly liberating manpower, and greatly reducing or even eliminating requirements for medical staff to master the knowledge of skin prints.

(e) Skin prints do not change with time, so the present invention is particularly suitable for infants. The sooner the application, the better the later intervention.

The present invention will be further described below in combination with specific Examples. It should be understood that these examples are only for illustrating the present invention and are not intended to limit the scope of the present invention. The experimental methods without specific conditions in the following examples generally follow the conventional conditions or the conditions recommended by the manufacturer.

Specimen Situation

The specimens of Down syndrome patients used in the present invention were 41 specimens from Hong Kong, 107 specimens from Taiwan and 108 specimens from Shanghai, respectively. The average age was less than 18 years old, and the female specimens accounted for about 39%. The healthy control group was consist of two groups of specimens, wherein one was the 400 Han religion specimens randomly selected in the Taizhou Healthy Population Tracking Survey (TZL), and the other was 400 Han specimens collected in Shanghai. The gender ratio of normal specimens was 1:1 (Table B).

TABLE B

| | Basic information of groups | | | | | |
|---|---|---|---|---|---|---|
| Group | Male N (%) | Average Age | Female N (%) | Average Age | All N | Average Age |
| Case_HK | 28(68.29%) | 15.28 | 13(31.71%) | 13.71 | 41 | 14.79 |
| Case_Taiwan | 59(55.14%) | 9.31 | 48(44.86%) | 9.32 | 107 | 9.32 |
| Case_Shanghai | 69(63.89%) | 16.36 | 39(36.11%) | 16.03 | 108 | 16.24 |
| All cases | 156(60.93%) | 13.5 | 100(39.07%) | 12.5 | 256 | 13.11 |
| Control_Taizhou | 200(50%) | 58.33 | 200(50%) | 59.08 | 400 | 58.705 |
| Control_Shanghai | 200(50%) | 21 | 200(50%) | 20 | 400 | 20.5 |
| All Controls | 400(50%) | 39.66 | 400(50%) | 39.54 | 800 | 39.6 |

Example 1 Division of Training Sets and Independent Verification Sets

The specimens of 5% (about 11 cases) of Down syndrome patients and 5% (about 40 cases) of normal control were randomly selected, thereby forming a machine learning independent verification data set (Test set). The remaining specimens (about 1005 cases) were used as Training data set (Training set) for model construction. When the specimens were randomly selected, the gender ratio of specimen was considered.

Example 2. Screening of Training Set Feature Variables

The important feature variables of the 56 skin print features for 1005 specimens were screened by following the important feature screening process in FIG. 1 (in the dashed box):

1. Chi-square test (categorical variable) and average t test (quantity variable) were used to test the difference between Down syndrome case group (case group) and normal control group (control). The features with no significant difference between the case group and the control group were removed.

2. The XGBoost machine learning algorithm was used to rank the feature items with significant differences between the case group and the control group obtained in Step 1, and the feature items with cumulative importance of more than 99% were retained.
3. Based on the correlation between the feature items retained in Step 2, the items with higher correlation (correlation coefficient >0.7) and having lower importance ranking were removed.
4. XGBoost was used to train and establish a model for the feature items retained in Step 3, thereby achieving classification based on combination of cases and controls. Further, 10-fold cross verification was used to test average accuracy and true positive rate (TPR), false negative rate (FNR) and other indicators of the model. The characteristic variable combination with the best effect to distinguish case specimen and control specimen was screened out.

Example 3. Verification of Independent Verification Sets

XGBoost was used to establish an optimal model that could distinguish case specimen and control specimen in the training set, and the model was applied to an independent verification test set having 51 specimens, and the average accuracy, true positive rate (TPR), false negative rate (FNR) and other indicators were calculated for screening Down syndrome specimen in the independent verification set by using this optimal combination of feature items In addition, in order to verify the robust of the model, support vector machine (SVM) (Suykens and Vandewalle, 1999) and linear discriminant analysis (LDA) (Mika et al., 1999) were also used to evaluate the screening effects for Down syndrome on independent specimen based on this combination of feature variables.

Results

1. The distribution profile of skin print features in normal control and in patients with Down syndrome was detailed described for the first time.

It was observed that, after the strict screening of 56 skin print features (Table A), 29 skin prints were found to have significant differences between Down syndrome patient group and the normal control group ($p<1\times10^{-4}$) (Table 1).

TABLE 1

Disease group and the results of the syndrome test results"

| No. | Skin Print features | Case_HK | Case_Taiwan | Group Case_Shanghai | Control_Taizhou | Control_Shanghai | P value |
|---|---|---|---|---|---|---|---|
| V1 | Arch % | 97.56 | 93.46 | 94.44 | 8.75 | 10.75 | $3.32 \times 10^{-135}$ |
|  | Loop % | 0 | 5.61 | 4.63 | 68 | 56.5 |  |
|  | Whorl % | 2.44 | 0.93 | 0.93 | 23.25 | 32.75 |  |
| V2 | non-real print-arch % | 97.56 | 98.13 | 100 | 89.75 | 91.25 | $6.35 \times 10^{-5}$ |
|  | real print % | 2.44 | 1.87 | 0 | 10.25 | 8.75 |  |
| V3 | non-real print-arch % | 60.98 | 48.6 | 56.48 | 50.5 | 50.75 | 0.389 |
|  | real print % | 39.02 | 51.4 | 43.52 | 49.5 | 49.25 |  |
| V4 | non-real print- arch % | 97.56 | 92.52 | 91.67 | 96.75 | 95 | 0.119 |
|  | real print % | 2.44 | 7.48 | 8.33 | 3.25 | 5 |  |
| V5 | non-real print- arch % | 78.05 | 71.03 | 72.22 | 65.75 | 92 | $3.16 \times 10^{-2}$ |
|  | real print % | 21.95 | 28.97 | 27.78 | 34.25 | 8 |  |
| V6 | non-real print- arch % | 100 | 100 | 100 | 99.75 | 99.5 | 0.773 |
|  | real print % | 0 | 0 | 0 | 0.25 | 0.5 |  |
| V7 | Arch % | 97.56 | 91.59 | 93.52 | 9.25 | 8.25 | $1.35 \times 10^{-139}$ |
|  | Loop % | 0 | 7.48 | 6.48 | 68 | 60.75 |  |
|  | Whorl % | 2.44 | 0.93 | 0 | 22.75 | 31 |  |
| V8 | non-real print-arch % | 97.56 | 97.2 | 99.07 | 92 | 89.75 | $5.08 \times 10^{-4}$ |
|  | real print % | 2.44 | 2.8 | 0.93 | 8 | 10.25 |  |
| V9 | non-real print-arch % | 63.41 | 52.34 | 56.48 | 48.25 | 46.5 | $1.37 \times 10^{-2}$ |
|  | real print % | 36.59 | 47.66 | 43.52 | 51.75 | 53.5 |  |
| V10 | non-real print-arch % | 95.12 | 87.85 | 82.41 | 95 | 93 | $3.9 \times 10^{-3}$ |
|  | real print % | 4.88 | 12.15 | 17.59 | 5 | 7 |  |
| V11 | non-real print-arch % | 65.85 | 74.77 | 73.15 | 61.75 | 86.25 | 0.681 |
|  | real print % | 34.15 | 25.23 | 26.85 | 38.25 | 13.75 |  |
| V12 | non-real print-arch % | 100 | 99.07 | 98.15 | 99.75 | 99.75 | 0.167 |
|  | real print % | 0 | 0.93 | 1.85 | 0.25 | 0.25 |  |
| V13 | arch % | 0 | 0.93 | 1.85 | 1 | 1.25 | $2.15 \times 10^{-3}$ |
|  | loop % | 85.37 | 85.98 | 81.48 | 76 | 70 |  |
|  | whorl % | 14.63 | 13.08 | 16.67 | 23 | 28.75 |  |
| V14 | arch % | 0 | 0.93 | 1.85 | 0.75 | 0.5 | $1.09 \times 10^{-15}$ |
|  | arch % | 65.85 | 64.49 | 65.74 | 36.25 | 34 |  |
|  | loop % | 34.15 | 34.58 | 32.41 | 63 | 65.5 |  |
| V15 | whorl % | 0 | 0 | 0 | 3.5 | 3 | $1.01 \times 10^{-25}$ |
|  | arch % | 90.24 | 90.65 | 90.74 | 54.75 | 49.5 |  |
|  | loop % | 9.76 | 9.35 | 9.26 | 41.75 | 47.5 |  |
| V16 | whorl % | 0 | 0.93 | 0.93 | 4.75 | 5.25 | $2.18 \times 10^{-39}$ |
|  | arch % | 97.56 | 92.52 | 94.44 | 49.25 | 41.25 |  |
|  | loop % | 2.44 | 6.54 | 4.63 | 46 | 53.5 |  |
| V17 | whorl % | 4.88 | 0.93 | 1.85 | 3.5 | 3.5 | $8.62 \times 10^{-10}$ |
|  | arch % | 70.73 | 64.49 | 59.26 | 41.5 | 38.25 |  |
|  | loop % | 24.39 | 34.58 | 38.89 | 55 | 58.25 |  |

TABLE 1-continued

Disease group and the results of the syndrome test results"

| No. | Skin Print features | Case_HK | Case_Taiwan | Case_Shanghai | Control_Taizhou | Control_Shanghai | P value |
|---|---|---|---|---|---|---|---|
| V18 | N | 41 | 107 | 108 | 400 | 400 | $1.28 \times 10^{-17}$ |
|  | Mean | 10.63 | 10.07 | 10.17 | 13.09 | 13.14 |  |
|  | Std Dev | 4.08 | 4.4 | 4.33 | 5.07 | 4.72 |  |
|  | Min-Max | 2-21 | 0-25 | 0-21 | 0-27 | 0-25 |  |
| V19 | N | 41 | 107 | 108 | 400 | 400 | $3.86 \times 10^{-36}$ |
|  | Mean | 12.44 | 11.08 | 10.71 | 16.26 | 16.39 |  |
|  | Std Dev | 4.39 | 5.23 | 5.1 | 5.79 | 5.03 |  |
|  | Min-Max | 5-24 | 0-28 | 0-24 | 0-28 | 0-30 |  |
| V20 | N | 41 | 107 | 108 | 400 | 400 | $1.75 \times 10^{-5}$ |
|  | Mean | 13 | 12.78 | 12.38 | 14.18 | 13.94 |  |
|  | STD DEV | 4.64 | 4.26 | 3.8 | 6.33 | 5.8 |  |
|  | MIN-MAX | 0-24 | 3-25 | 4-25 | 0-26 | 0-36 |  |
| V21 | N | 41 | 107 | 108 | 400 | 400 | $8.53 \times 10^{-4}$ |
|  | Mean | 14.46 | 11.52 | 11.38 | 13.42 | 12.96 |  |
|  | Std Dev | 4.78 | 4.27 | 4.76 | 6.51 | 5.93 |  |
|  | Min-Max | 4-24 | 0-26 | 0-25 | 0-28 | 0-28 |  |
| V22 | N | 41 | 107 | 108 | 400 | 400 | 0.854 |
|  | Mean | 17.44 | 16.4 | 15.26 | 16.02 | 15.94 |  |
|  | Std Dev | 6.95 | 6.46 | 5.8 | 6.32 | 5.78 |  |
|  | Min-Max | 0-29 | 0-30 | 0-28 | 0-28 | 0-28 |  |
| V23 | Non-simian crease % | 36.59 | 56.07 | 37.96 | 90.5 | 86.25 | $5.46 \times 10^{-46}$ |
|  | simian crease hand % | 63.41 | 43.93 | 62.04 | 9.5 | 13.75 |  |
| V24 | c\d\t | 73.17 | 87.85 | 90.74 | 93.25 | 89.75 | 0.115 |
|  | lack of c area | 26.83 | 10.28 | 8.33 | 5.75 | 9.25 |  |
|  | lack of d area | 0 | 1.87 | 0.93 | 0.75 | 0.5 |  |
|  | lack of t area | 0 | 0 | 0 | 0.25 | 0.5 |  |
| V25 | N | 41 | 107 | 108 | 400 | 400 | 0.97 |
|  | Mean | 43.1 | 40.89 | 36.93 | 41.45 | 37.76 |  |
|  | Std Dev | 6.2 | 5.29 | 5.53 | 3.28 | 4.31 |  |
|  | Min-Max | 21-52 | 32-72 | 15-53 | 32-49 | 25-52 |  |
| V26 | non-real print-arch % | 95.12 | 95.33 | 98.15 | 84 | 85 | $8.46 \times 10^{-7}$ |
|  | real print % | 4.88 | 4.67 | 1.85 | 16 | 15 |  |
| V27 | non-real print-arch % | 90.24 | 98.13 | 99.07 | 99.25 | 99.75 | $2.32 \times 10^{-2}$ |
|  | real print % | 9.76 | 1.87 | 0.93 | 0.75 | 0.25 |  |
| V28 | non-real print-arch % | 70.73 | 54.21 | 53.7 | 90 | 93.5 | $8.71 \times 10^{-36}$ |
|  | real print % | 29.27 | 45.79 | 46.3 | 10 | 6.5 |  |
| V29 | non-real print-arch % | 68.29 | 62.62 | 63.89 | 12.5 | 21.25 | $8.02 \times 10^{-45}$ |
|  | real print % | 31.71 | 37.38 | 36.11 | 87.5 | 78.75 |  |
| V30 | non-real print-arch % | 100 | 99.07 | 100 | 100 | 100 | 0.55 |
|  | real print % | 0 | 0.93 | 0 | 0 | 0 |  |
| V31 | non-real print-arch % | 80.49 | 89.72 | 89.81 | 98.5 | 90 | $9 \times 10^{-4}$ |
|  | real print % | 19.51 | 10.28 | 10.19 | 1.5 | 10 |  |
| V32 | non-real print-arch % | 51.22 | 49.53 | 51.85 | 79.75 | 81.5 | $4.58 \times 10^{-20}$ |
|  | real print % | 48.78 | 50.47 | 48.15 | 20.25 | 18.5 |  |
| V33 | N | 41 | 107 | 108 | 400 | 400 | $2.46 \times 10^{-48}$ |
|  | Mean | 63.29 | 60.24 | 59.76 | 41.84 | 39.79 |  |
|  | Std Dev | 17.52 | 14.53 | 18.69 | 6.38 | 5.94 |  |
|  | Min-Max | 35-101 | 33-94 | 0-106 | 0-66 | 0-58 |  |
| V34 | arch % | 0 | 0.93 | 1.85 | 2 | 2.75 | $2.03 \times 10^{-16}$ |
|  | loop % | 65.85 | 71.03 | 60.19 | 35.75 | 32 |  |
|  | whorl % | 34.15 | 28.04 | 37.96 | 62.25 | 65.25 |  |
| V35 | arch % | 0 | 0.93 | 0 | 5.25 | 3.75 | $1.92 \times 10^{-42}$ |
|  | loop % | 97.56 | 95.33 | 94.44 | 47.25 | 43.5 |  |
|  | whorl % | 2.44 | 3.74 | 5.56 | 47.5 | 52.75 |  |
| V36 | arch % | 0 | 0 | 0 | 2.25 | 2 | $2.62 \times 10^{-19}$ |
|  | loop % | 97.56 | 91.59 | 87.04 | 58.75 | 59.25 |  |
|  | whorl % | 2.44 | 8.41 | 12.96 | 39 | 38.75 |  |
| V37 | arch % | 0 | 0.93 | 0.93 | 0.75 | 0.75 | $2.22 \times 10^{-24}$ |
|  | loop % | 73.17 | 71.03 | 61.11 | 34 | 27.5 |  |
|  | whorl % | 26.83 | 28.04 | 37.96 | 65.25 | 71.75 |  |
| V38 | arch % | 0 | 0 | 0 | 1 | 1.25 | $7.51 \times 10^{-4}$ |
|  | loop % | 75.61 | 79.44 | 82.41 | 68.5 | 66 |  |
|  | whorl % | 24.39 | 20.56 | 17.59 | 30.5 | 32.75 |  |
| V39 | N | 41 | 107 | 108 | 400 | 400 | 0.605 |
|  | Mean | 19.83 | 17.73 | 16.4 | 17.07 | 17.51 |  |
|  | Std Dev | 5.65 | 5.6 | 5.71 | 6.15 | 5.78 |  |
|  | Min-Max | 8-29 | 0-30 | 0-32 | 0-29 | 0-29 |  |
| V40 | N | 41 | 107 | 108 | 400 | 400 | $7.38 \times 10^{-3}$ |
|  | Mean | 14.51 | 12.07 | 11.69 | 13.39 | 13.24 |  |
|  | Std Dev | 4.93 | 4.08 | 4.21 | 6.69 | 5.87 |  |
|  | Min-Max | 7-26 | 0-22 | 3-24 | 0-28 | 0-29 |  |
| V41 | N | 41 | 107 | 108 | 400 | 400 | $1.45 \times 10^{-3}$ |
|  | Mean | 13.78 | 11.93 | 12.19 | 13.34 | 13.34 |  |
|  | Std Dev | 3.94 | 3.61 | 4.02 | 6.44 | 5.5 |  |
|  | Min-Max | 2-21 | 1-21 | 2-24 | 0-28 | 0-32 |  |

TABLE 1-continued

Disease group and the results of the syndrome test results"

| No. | Skin Print features | Case_HK | Case_Taiwan | Case_Shanghai | Control_Taizhou | Control_Shanghai | P value |
|---|---|---|---|---|---|---|---|
| V42 | N | 41 | 107 | 108 | 400 | 400 | $5.02 \times 10^{-36}$ |
|  | Mean | 13.05 | 11.12 | 10.56 | 15.9 | 16.26 |  |
|  | Std Dev | 4.75 | 4.93 | 4.45 | 5.84 | 4.85 |  |
|  | Min-Max | 2-23 | 0-28 | 0-24 | 0-28 | 0-31 |  |
| V43 | N | 41 | 107 | 108 | 400 | 400 | $8.48 \times 10^{-18}$ |
|  | Mean | 11.71 | 9.82 | 9.9 | 13.29 | 12.77 |  |
|  | Std Dev | 4.98 | 3.75 | 4.06 | 5.36 | 4.63 |  |
|  | Min-Max | 1-22 | 3-22 | 2-22 | 0-26 | 0-23 |  |
| V44 | Non-simian crease % | 34.15 | 47.66 | 48.15 | 93.5 | 85.25 | $1.03 \times 10^{-46}$ |
|  | Simian crease hand % | 65.85 | 52.34 | 51.85 | 6.5 | 14.75 |  |
| V45 | c\d\t % | 90.24 | 90.65 | 89.81 | 98.25 | 93 | $8.21 \times 10^{-3}$ |
|  | lack of c area % | 9.76 | 9.35 | 9.26 | 1.25 | 6.5 |  |
|  | lack of d area % | 0 | 0 | 0.93 | 0.25 | 0.25 |  |
|  | lack of t area % | 0 | 0 | 0 | 0.25 | 0.25 |  |
| V46 | N | 41 | 107 | 108 | 400 | 400 | 0.786 |
|  | Mean | 42.34 | 40.06 | 36.53 | 40.74 | 37.43 |  |
|  | Std Dev | 3.75 | 3.65 | 6.58 | 3.87 | 4.84 |  |
|  | Min-Max | 30-49 | 31-50 | 0-52 | 1-49 | 4-51 |  |
| V47 | non-real print-arch % | 100 | 97.2 | 100 | 94.5 | 93.75 | $4.77 \times 10^{-3}$ |
|  | real print % | 0 | 2.8 | 0 | 5.5 | 6.25 |  |
| V48 | non-real print-arch % | 95.12 | 99.07 | 98.15 | 96.25 | 99 | 0.667 |
|  | real print % | 4.88 | 0.93 | 1.85 | 3.75 | 1 |  |
| V49 | non-real print-arch % | 41.46 | 42.06 | 36.11 | 76 | 81.5 | $7.93 \times 10^{-30}$ |
|  | real print % | 58.54 | 57.94 | 63.89 | 24 | 18.5 |  |
| V50 | non-real print-arch % | 65.85 | 65.42 | 70.37 | 20.25 | 30.25 | $3.36 \times 10^{-32}$ |
|  | real print % | 34.15 | 34.58 | 29.63 | 79.75 | 69.75 |  |
| V51 | non-real print-arch % | 100 | 99.07 | 100 | 100 | 100 | 0.55 |
|  | real print % | 0 | 0.93 | 0 | 0 | 0 |  |
| V52 | non-real print-arch % | 92.68 | 92.52 | 97.22 | 98.75 | 91.5 | 0.717 |
|  | real print % | 7.32 | 7.48 | 2.78 | 1.25 | 8.5 |  |
| V53 | non-real print-arch % | 46.34 | 49.53 | 54.63 | 80.5 | 84.5 | $1.77 \times 10^{-22}$ |
|  | real print % | 53.66 | 50.47 | 45.37 | 19.5 | 15.5 |  |
| V54 | N | 41 | 107 | 108 | 400 | 400 | $2.93 \times 10^{-43}$ |
|  | Mean | 60 | 59.22 | 58.13 | 41.77 | 39.88 |  |
|  | Std Dev | 15.79 | 14.95 | 18.22 | 5.72 | 5.33 |  |
|  | Min-Max | 26-94 | 34-101 | 0-105 | 0-61 | 0-60 |  |
| V55 | 2 inter-finger folds % | 46.34 | 39.25 | 62.96 | 100 | 100 | $4.56 \times 10^{-97}$ |
|  | 2 inter-finger folds with a bent little finger % | 0 | 26.17 | 12.04 | 0 | 0 |  |
|  | 1 inter-finger fold | 53.66 | 34.58 | 25 | 0 | 0 |  |
| V56 | 2 inter-finger folds % | 43.9 | 39.25 | 61.11 | 100 | 100 | $7.83 \times 10^{-99}$ |
|  | 2 inter-finger fold with a bent little finger % | 0 | 28.97 | 10.19 | 0 | 0 |  |
|  | 1 inter-finger fold | 56.1 | 31.78 | 28.7 | 0 | 0 |  |

Note:
The last column was P value of difference verification for each skin print feature between the disease group and the control group, the chi-square test was used for the classification of variables, and an average t-test was used for inspection of continuous variables. The bold portions were skin print feature items having a significant difference between the disease group and the control group ($P < 1 \times 10^{-4}$).

2. The machine learning methods were used for the first time to rank importance of skin print features which were significant abnormal in patients with Down syndrome. The top 6 features were used to construct an assisted screening system of Down syndrome, with accuracy of more than 98% and a missed diagnosis rate thereof was controlled around 6-7%

Figure 2:
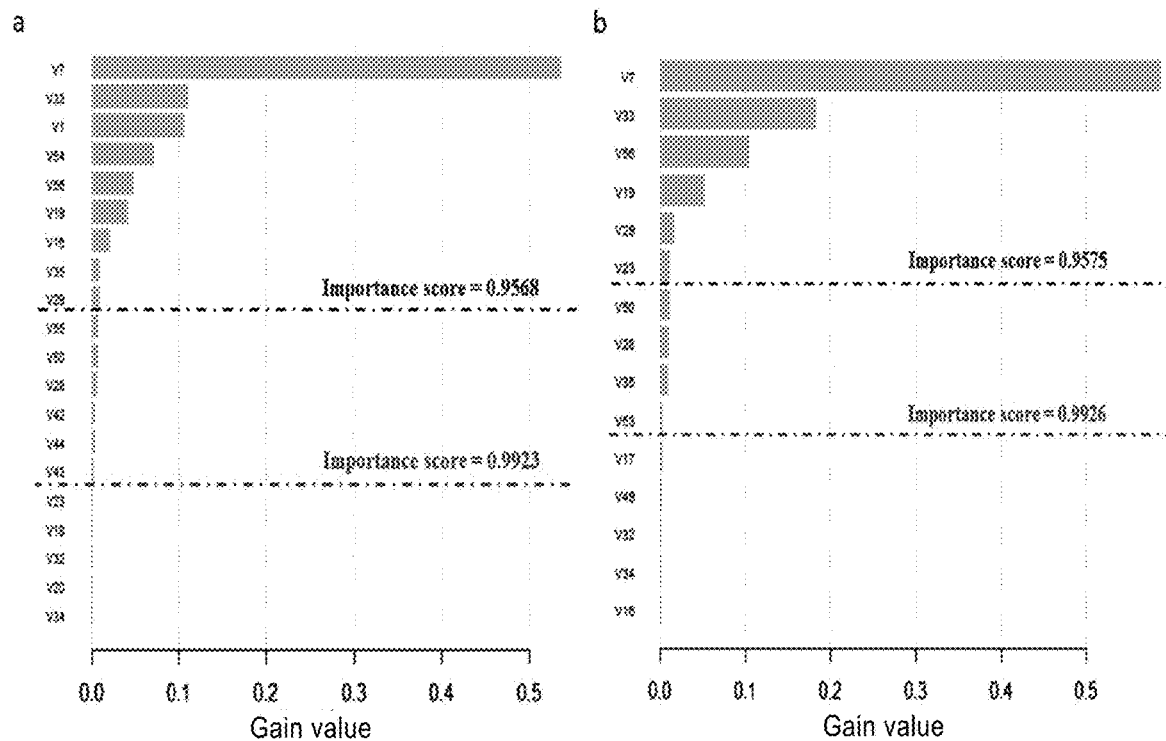

The importance of skin print features in patient with Down syndrome and the control group was ranked by using XGBoost. As a result, it was found that the cumulative importance of the top 15 skin print features reached 99% (FIG. 2A, red dashed line).

Next, the inventors analyzed 29 skin print features whether there was a pairwise correlation. The skin print features of the top 15 feature items in the importance ranking which had a coefficient of correlation higher than 0.7 were shown in Table C. The skin print features having a coefficient of correlation above 0.7 with the skin print features in first column were indicated in the third column of Table C. Further, the importance Gain value of the third column skin print features was lower than that of the corresponding features in the first column. For example, the correlation coefficient between V7 or the pattern on the ball of right foot and V1 or the pattern on the ball of left foot was 0.797, and importance Gain value of V1 was lower than that of V7.

TABLE C

Skin print features highly related to the top 15 features in the importance ranking

| Feature | Gain value | Feature variable with a Gain Value less than that of the feature in 1st column and with a correlation coefficient of 0.7 or above with the feature in 1st column | correlation coefficient between 1st column and 3rd column |
|---|---|---|---|
| V7 | 0.53697 | V1 | 0.7970 |
| V33 | 0.111402 | V54 | 0.7697 |
| V1 | 0.106605 | — | |
| V54 | 0.071919 | — | |
| V56 | 0.04839 | V55 | 0.9580 |
| V19 | 0.042143 | V20 | 0.7343 |
| V19 | 0.042143 | V42 | 0.7900 |
| V16 | 0.020714 | — | |
| V35 | 0.009428 | — | |
| V29 | 0.00927 | — | |
| V55 | 0.00873 | — | |
| V50 | 0.007637 | — | |
| V28 | 0.007492 | — | |
| V42 | 0.0042 | V43 | 0.7354 |
| V44 | 0.00381 | — | |
| V43 | 0.003573 | V18 | 0.7243 |

After the skin print features having a correlation coefficient above 0.7 were removed based on the importance ranking, the remaining 22 skin print features were ranked again for importance, and the results showed that the cumulative importance ranking of the top 10 skin print features could reach 99%. (FIG. 2b, red dashed line), the cumulative importance ranking of the top 6 skin print features was higher than 95% (FIG. 2B, blue dashed line).

Figure 3:
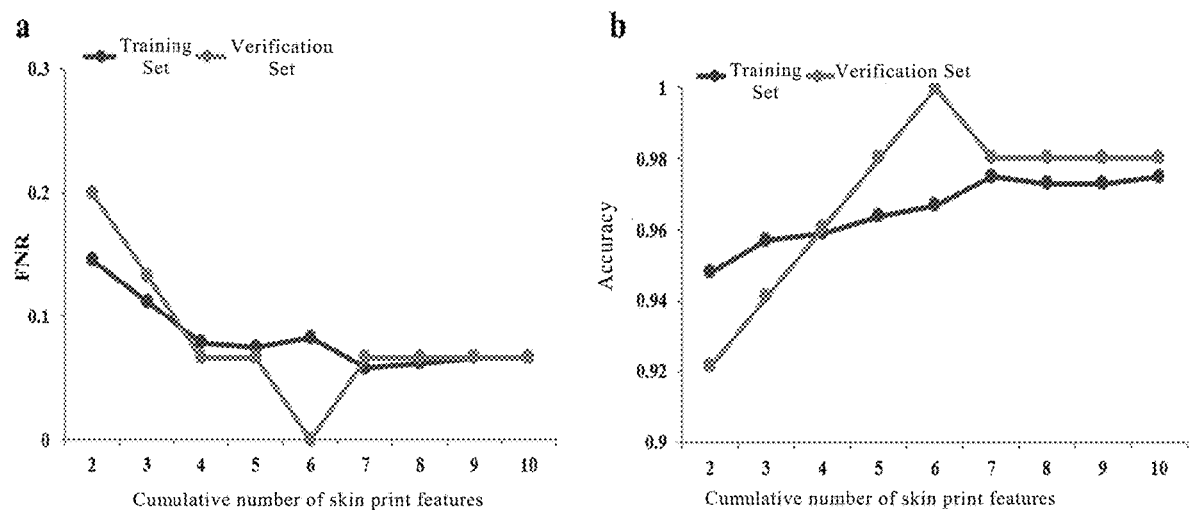

According to the importance ranking of the skin prints (FIG. 2b), the assisted screening system for Down syndrome was established by using XGBoost method training based on cumulative sets, and an embedded 10-fold cross validation was used to evaluate the system on the independent verification specimens. As a result, it was found that the early screening system for Down syndrome constructed by the top 6 skin print features (V7—pattern on the ball of right foot; V33—left hand atd angle; V56-D5R inter-finger fold; V19-D4L crest line; V29—left hand print in IV zone; V23—whether left hand has simian crease) had a higher accuracy (98%) and a lower false negative rate (6.67%) (see FIG. 3, Table 2).

TABLE 2

Model construction based on training set via XGBoost and verification on independent specimens

| | 2 items | 3 items | 4 items | 5 items | 6 items | 7 items | 8 items | 9 items | 10 items | REED-4 |
|---|---|---|---|---|---|---|---|---|---|---|
| Training set (n = 1005) | | | | | | | | | | |
| AUC | 0.9827 | 0.9891 | 0.9925 | 0.9949 | 0.9955 | 0.9957 | 0.9958 | 0.9963 | 0.9956 | 0.9852 |
| TPR | 0.8543 | 0.8878 | 0.9212 | 0.9252 | 0.9172 | 0.9418 | 0.9377 | 0.9337 | 0.9337 | 0.9168 |
| FNR | 0.1457 | 0.1122 | 0.0788 | 0.0748 | 0.0828 | 0.0582 | 0.0623 | 0.0663 | 0.0663 | 0.0832 |
| FPR | 0.0223 | 0.021 | 0.0289 | 0.0236 | 0.017 | 0.0144 | 0.0157 | 0.0144 | 0.0118 | 0.0314 |
| precision | 0.9269 | 0.9367 | 0.9135 | 0.9291 | 0.9473 | 0.9553 | 0.953 | 0.9554 | 0.9631 | 0.9056 |
| accuracy | 0.9481 | 0.9572 | 0.9591 | 0.9641 | 0.9671 | 0.9751 | 0.9731 | 0.9731 | 0.9751 | 0.9562 |
| specificity | 0.9777 | 0.979 | 0.9711 | 0.9764 | 0.983 | 0.9856 | 0.9843 | 0.9856 | 0.9882 | 0.9686 |
| F-Measure | 0.4434 | 0.4548 | 0.4580 | 0.463 | 0.4653 | 0.4740 | 0.472 | 0.4717 | 0.4737 | 0.4549 |
| Verification set (N = 51) | | | | | | | | | | |
| AUC | 0.9796 | 0.9889 | 0.9944 | 0.9981 | 1 | 0.9981 | 1 | 1 | 1 | 1 |
| TPR | 0.8 | 0.8667 | 0.9333 | 0.9333 | 1 | 0.9333 | 0.9333 | 0.9333 | 0.9333 | 0.8667 |
| FNR | 0.2 | 0.1333 | 0.0667 | 0.0667 | 0 | 0.0667 | 0.0667 | 0.0667 | 0.0667 | 0.1333 |
| FPR | 0.0278 | 0.0278 | 0.0278 | 0 | 0 | 0 | 0 | 0 | 0 | 0 |
| precision | 0.9231 | 0.9286 | 0.9333 | 1 | 1 | 1 | 1 | 1 | 1 | 1 |
| accuracy | 0.9216 | 0.9412 | 0.9608 | 0.9804 | 1 | 0.9804 | 0.9804 | 0.9804 | 0.9804 | 0.9608 |
| specificity | 0.9722 | 0.9722 | 0.9722 | 1 | 1 | 1 | 1 | 1 | 1 | 1 |
| F-Measure | 0.4286 | 0.4483 | 0.4667 | 0.4828 | 0.5 | 0.4828 | 0.4828 | 0.4828 | 0.4828 | 0.4643 |

Note:
AUC (Area under Curve);
TPR (True Positive Rate);
FNR (False Negative Rate);
FPR (False Positive Rate);
precision; accuracy; specificity;
The order of the six skin print feature items was: V7\V33\V56\V19\V29\V23. "The top 2 items" were "V7/V33", "the top 3 items" were "V7\V33\V56", and so on.

Figure 4:
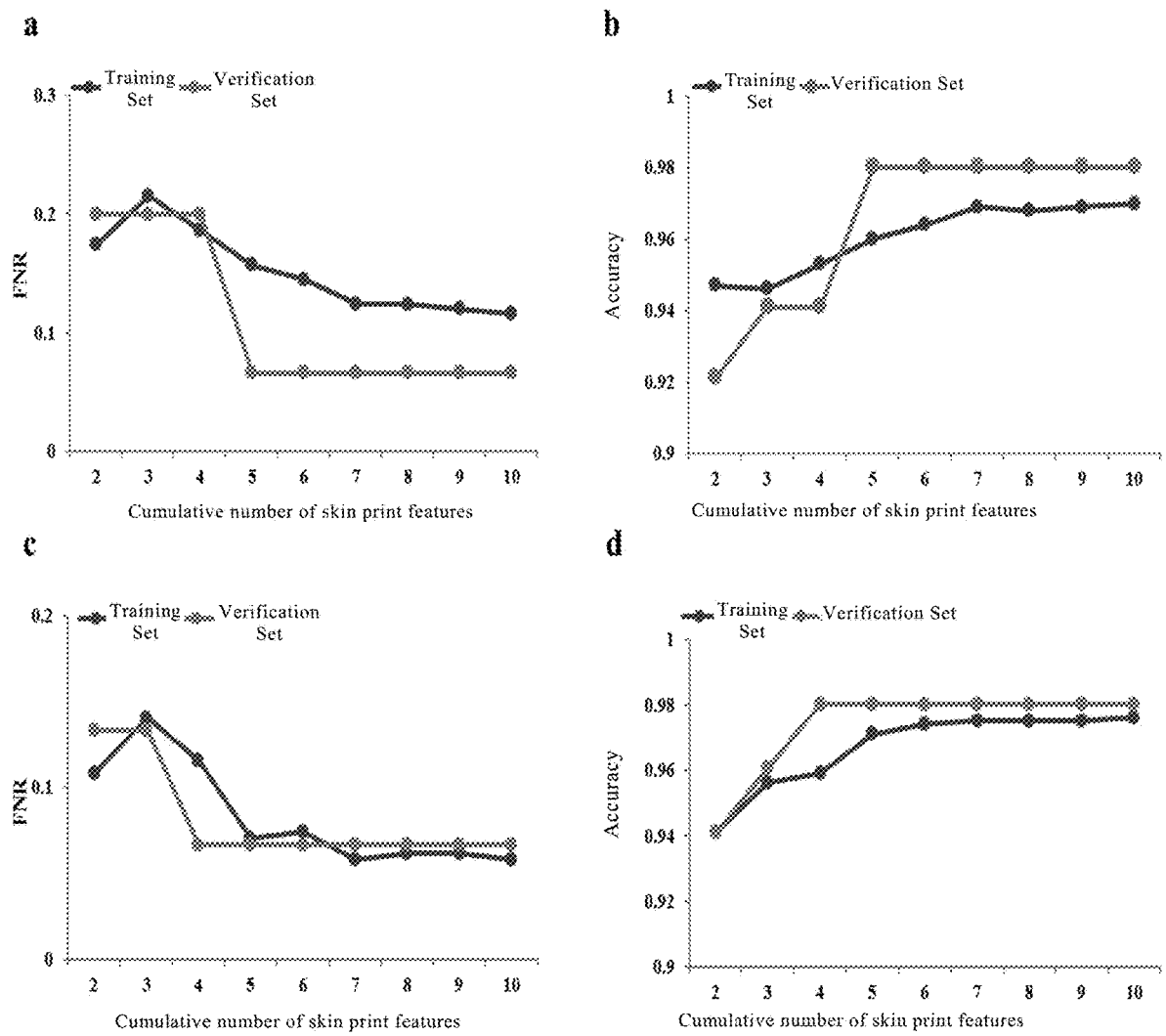
FIG. 4 shows the performance of the number of features and training set and independent test set under the LDA training and SVM training, wherein in the LDA method (FIGS. 4a and 4b) and SVM method (FIGS. 4c and 4d), the false negative rate (FIG. 4a, FIG. 4c) and accuracy (FIG. 4b, FIG. 4d) are changed.

3. Different machine learning methods were used in comparison to verify the robustness of the skin print screening system constructed in the present invention In order to verify the robustness of the combination of skin print features screened out by XGBoost, in the present invention, LDA (Lienar Discrriminant Analysis) and SVM (support vector machine) model were used to carry out training on training set and prediction on independent verification set. When the linear discriminant analysis was used to construct a training model based on the training set and when feature variables were increased to include the 6th item, the training set exhibited a low false negative rate (14.5%) and high accuracy (96.4%). The false negative rate was 6.7% and the accuracy was 98% in the independent verification set (Table 3, FIGS. 4a-b). The screening of the skin print via SVM also showed that the 6 skin print feature items had similar discrimination abilities (Table 4, FIGS. 4c-d). We found that XGBoost exhibited significant advantages in our data, with lower false negative rates (less than 6.7%, close to 0) by comparing the results of three models established by XGBoost, LDA and SVM.

For the specific value of evaluation indicators in the LDA method and SVM method for training set and verification set, please refer to Table 3 and Table 4.

TABLE 3

Model construction based on training set via Linear discriminant analysis (LDA) and verification on independent specimens

| | 2 items | 3 items | 4 items | 5 items | 6 items | 7 items | 8 items | 9items | 10 items | REED-4 |
|---|---|---|---|---|---|---|---|---|---|---|
| Training set (n = 1005) | | | | | | | | | | |
| AUC | 0.9795 | 0.9878 | 0.9914 | 0.9942 | 0.9944 | 0.995 | 0.9948 | 0.9946 | 0.9955 | 0.9817 |
| TPR | 0.8253 | 0.7847 | 0.8135 | 0.8425 | 0.855 | 0.8757 | 0.8755 | 0.8797 | 0.8837 | 0.8293 |
| FNR | 0.1747 | 0.2153 | 0.1865 | 0.1575 | 0.145 | 0.1243 | 0.1245 | 0.1203 | 0.1163 | 0.1707 |
| FPR | 0.0145 | 0.0026 | 0.0026 | 0.0026 | 0.0013 | 0.0013 | 0.0026 | 0.0026 | 0.0026 | 0.0236 |
| precision | 0.9532 | 0.9897 | 0.9902 | 0.99 | 0.9957 | 0.9947 | 0.9908 | 0.9908 | 0.9904 | 0.9173 |
| accuracy | 0.9471 | 0.9463 | 0.9532 | 0.9602 | 0.9642 | 0.9691 | 0.9681 | 0.9691 | 0.9701 | 0.9412 |
| specificity | 0.9855 | 0.9974 | 0.9974 | 0.9974 | 0.9987 | 0.9987 | 0.9974 | 0.9974 | 0.9974 | 0.9764 |
| F-Measure | 0.4406 | 0.437 | 0.4457 | 0.4546 | 0.4594 | 0.4652 | 0.4642 | 0.4655 | 0.4665 | 0.4349 |
| Verification set (n = 51) | | | | | | | | | | |
| AUC | 0.9898 | 0.9944 | 0.9981 | 0.9944 | 1 | 1 | 1 | 1 | 1 | 1 |
| TPR | 0.8 | 0.8 | 0.8 | 0.9333 | 0.9333 | 0.9333 | 0.9333 | 0.9333 | 0.9333 | 0.8667 |
| FNR | 0.2 | 0.2 | 0.2 | 0.0667 | 0.0667 | 0.0667 | 0.0667 | 0.0667 | 0.0667 | 0.1333 |
| FPR | 0.0278 | 0 | 0 | 0 | 0 | 0 | 0 | 0 | 0 | 0 |
| precision | 0.9231 | 1 | 1 | 1 | 1 | 1 | 1 | 1 | 1 | 1 |
| accuracy | 0.9216 | 0.9412 | 0.9412 | 0.9804 | 0.9804 | 0.9804 | 0.9804 | 0.9804 | 0.9804 | 0.9608 |
| specificity | 0.9722 | 1 | 1 | 1 | 1 | 1 | 1 | 1 | 1 | 1 |
| F-Measure | 0.4286 | 0.4444 | 0.4444 | 0.4828 | 0.4828 | 0.4828 | 0.4828 | 0.4828 | 0.4828 | 0.4643 |

TABLE 4

Model construction based on training set via SVM and verification on independent specimens

| | 2 items | 3 items | 4 items | 5 items | 6 items | 7 items | 8 items | 9 items | 10 items | REED-4 |
|---|---|---|---|---|---|---|---|---|---|---|
| Training set (n = 1005) | | | | | | | | | | |
| AUC | 0.9791 | 0.9869 | 0.9904 | 0.9942 | 0.9935 | 0.9937 | 0.994 | 0.9941 | 0.9953 | 0.9806 |
| TPR | 0.8917 | 0.8592 | 0.8838 | 0.9293 | 0.9257 | 0.942 | 0.9378 | 0.9378 | 0.942 | 0.9083 |
| FNR | 0.1083 | 0.1408 | 0.1162 | 0.0707 | 0.0743 | 0.058 | 0.0622 | 0.0622 | 0.058 | 0.0917 |
| FPR | 0.0432 | 0.0131 | 0.0171 | 0.0157 | 0.0105 | 0.0144 | 0.0131 | 0.0131 | 0.0131 | 0.0445 |
| precision | 0.8784 | 0.9589 | 0.9449 | 0.9506 | 0.9669 | 0.9552 | 0.9603 | 0.9603 | 0.9605 | 0.8683 |
| accuracy | 0.9412 | 0.9562 | 0.9591 | 0.9711 | 0.9741 | 0.9751 | 0.9751 | 0.9751 | 0.9761 | 0.9442 |
| specificity | 0.9568 | 0.9869 | 0.9829 | 0.9843 | 0.9895 | 0.9856 | 0.9869 | 0.9869 | 0.9869 | 0.9555 |
| F-Measure | 0.4404 | 0.452 | 0.456 | 0.4694 | 0.4723 | 0.4738 | 0.474 | 0.474 | 0.475 | 0.4431 |
| Verification set (N = 51) | | | | | | | | | | |
| AUC | 0.9898 | 0.9944 | 0.9981 | 0.9963 | 1 | 1 | 1 | 1 | 0.9981 | 1 |
| TPR | 0.8667 | 0.8667 | 0.9333 | 0.9333 | 0.9333 | 0.9333 | 0.9333 | 0.9333 | 0.9333 | 0.9333 |
| FNR | 0.1333 | 0.1333 | 0.0667 | 0.0667 | 0.0667 | 0.0667 | 0.0667 | 0.0667 | 0.0667 | 0.0667 |
| FPR | 0.0278 | 0 | 0 | 0 | 0 | 0 | 0 | 0 | 0 | 0 |
| precision | 0.9286 | 1 | 1 | 1 | 1 | 1 | 1 | 1 | 1 | 1 |
| accuracy | 0.9412 | 0.9608 | 0.9804 | 0.9804 | 0.9804 | 0.9804 | 0.9804 | 0.9804 | 0.9804 | 0.9804 |
| specificity | 0.9722 | 1 | 1 | 1 | 1 | 1 | 1 | 1 | 1 | 1 |
| F-Measure | 0.4483 | 0.4643 | 0.4828 | 0.4828 | 0.4828 | 0.4828 | 0.4828 | 0.4828 | 0.4828 | 0.4828 |

4. By comparing assisted screening systems for Down syndrome skin print features which were constructed based on foot prints or hand prints only, it was found that the best scheme should combine foot prints and hand prints.

In the present invention, 56 skin print features for each individual were read, wherein 12 items were foot print features, 44 items were finger print features and palm print features. If only the finger print, palm print or foot print was collected due to limitation, what kind of effects could a diagnosis system which was only established based on the finger print, palm print or foot print achieve? In the present invention, assisted screening systems for Down syndrome were constructed based on only finger print and palm print features, or only the footprint features, respectively.

According to the same feature variable screening scheme (See method and Step 2), the variable screening was performed on 44 skin print features of finger print and palm print, and the 20 items were screened out. It was found that the cumulative importance of the top 13 feature items was more than 99%, and the cumulative importance of the top 8 features was over 96% (FIG. 5a) by ranking the cumulative importance for 20 features. It should be noted that the top 5 features screened out by only using finger print and palm print features were all in the features of result 2 of the assisted screening system constructed by using finger print, palm print, and foot print features. The only difference between the system of the result 2 comprised V7—pattern on the ball of right foot. Therefore, it indicated that these 5 finger print and palm print features had big contribution for the construction of an assisted screening system.

Figure 5:
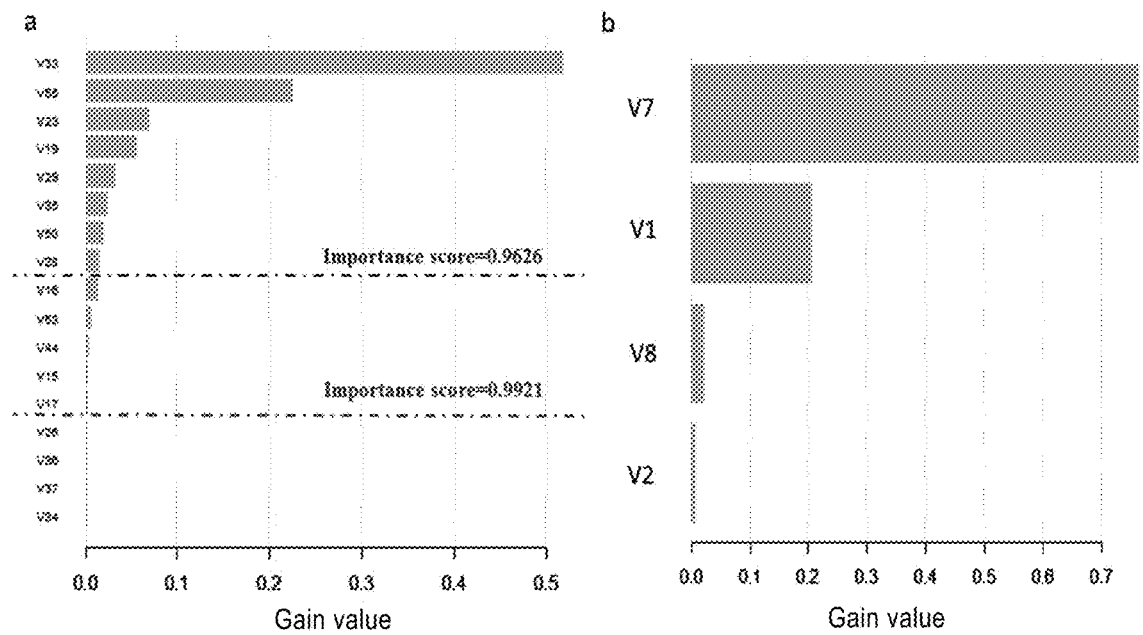
FIG. 5A shows the importance ranking of the finger and palm print feature variables.
FIG. 5b shows the importance ranking of the foot print.

Among the 12 foot print features, after removing the features with no significant difference between the patient group and the control group, only 4 features were the remained, including pattern on the ball of feet (V1\V7) and the inter-finger print in II zone (V2\V8), and importance ranking thereof was listed in FIG. 5b.

The XGBoost method was used to construct an assisted screening system based only on finger and palm print features. Using the top 8-10 finger and palm print features, the missed diagnosis rate could be controlled at 6%-7%, and the accuracy was 96% (Table 5, FIG. 6). This performance was only equivalent to the results of comprehensive use of the top four finger, palm, and feet print features (Table 2, FIG. 3).

TABLE 5

Model construction based on training set of only finger and palm print features via XGBoost and verification on independent specimens

|  | 1 item | 2 items | 3 items | 4 items | 5 items | 6 items | 7 items | 8 items | 9 items | 10 items |
|---|---|---|---|---|---|---|---|---|---|---|
| Training set (N = 1005) | | | | | | | | | | |
| AUC | 0.8748 | 0.9225 | 0.9448 | 0.9625 | 0.9793 | 0.9805 | 0.9817 | 0.9819 | 0.9860 | 0.9852 |
| TPR | 0.5980 | 0.7638 | 0.7888 | 0.8343 | 0.8633 | 0.8675 | 0.8468 | 0.8592 | 0.8715 | 0.8880 |
| FNR | 0.4020 | 0.2362 | 0.2112 | 0.1657 | 0.1367 | 0.1325 | 0.1532 | 0.1408 | 0.1285 | 0.1120 |
| FPR | 0.0131 | 0.0131 | 0.0079 | 0.0209 | 0.0183 | 0.0222 | 0.0235 | 0.0301 | 0.0274 | 0.0235 |
| precision | 0.9347 | 0.9488 | 0.9709 | 0.9272 | 0.9376 | 0.9257 | 0.9223 | 0.9028 | 0.9121 | 0.9251 |
| accuracy | 0.8936 | 0.9334 | 0.9433 | 0.9443 | 0.9532 | 0.9512 | 0.9453 | 0.9433 | 0.9483 | 0.9552 |
| specificity | 0.9869 | 0.9869 | 0.9921 | 0.9791 | 0.9817 | 0.9778 | 0.9765 | 0.9699 | 0.9726 | 0.9765 |
| F-Measure | 0.3629 | 0.4223 | 0.4342 | 0.4387 | 0.4490 | 0.4473 | 0.4405 | 0.4397 | 0.4451 | 0.4524 |
| Verification set (N = 51) | | | | | | | | | | |
| AUC | 0.8565 | 0.9065 | 0.9556 | 0.9407 | 0.9861 | 0.9898 | 0.9815 | 0.9778 | 0.9852 | 0.9889 |
| TPR | 0.6000 | 0.8000 | 0.8000 | 0.8667 | 0.8667 | 0.8667 | 0.8667 | 0.9333 | 0.8667 | 0.9333 |
| FNR | 0.4000 | 0.2000 | 0.2000 | 0.1333 | 0.1333 | 0.1333 | 0.1333 | 0.0667 | 0.1333 | 0.0667 |
| FPR | 0.0556 | 0.0556 | 0.0000 | 0.0000 | 0.0278 | 0.0278 | 0.0278 | 0.0556 | 0.0556 | 0.0278 |
| precision | 0.8182 | 0.8571 | 1.0000 | 1.0000 | 0.9286 | 0.9286 | 0.9286 | 0.8750 | 0.8667 | 0.9333 |
| accuracy | 0.8431 | 0.9020 | 0.9412 | 0.9608 | 0.9412 | 0.9412 | 0.9412 | 0.9412 | 0.9216 | 0.9608 |
| specificity | 0.9444 | 0.9444 | 1.0000 | 1.0000 | 0.9722 | 0.9722 | 0.9722 | 0.9444 | 0.9444 | 0.9722 |
| F-Measure | 0.3462 | 0.4138 | 0.4444 | 0.4643 | 0.4483 | 0.4483 | 0.4483 | 0.4516 | 0.4333 | 0.4667 |

Because there were only 4 foot print feature items with significant difference between the Down syndrome patient group and the control group, if only the foot print features was used to construct an assisted screening system, it was found that the highest accuracy rate in the independent verification set was 94%, and there were more than 5% false positives rate (Table 6).

TABLE 6

Model construction based on training set of only foot print features via XGBoost and verification on independent specimens

|  | 1 item | 2 items | 3 items | 4 items |
|---|---|---|---|---|
| Training set (N = 1005) |  |  |  |  |
| AUC | 0.9274 | 0.9480 | 0.9540 | 0.9551 |
| TPR | 0.9292 | 0.9292 | 0.9083 | 0.9083 |
| FNR | 0.0708 | 0.0708 | 0.0917 | 0.0917 |
| FPR | 0.0864 | 0.0511 | 0.0406 | 0.0445 |
| precision | 0.7774 | 0.8565 | 0.8783 | 0.8709 |
| accuracy | 0.9173 | 0.9442 | 0.9472 | 0.9442 |
| specificity | 0.9136 | 0.9489 | 0.9594 | 0.9555 |
| F-Measure | 0.4224 | 0.4446 | 0.4458 | 0.4434 |
| Verification set (N = 51) |  |  |  |  |
| AUC | 0.9444 | 0.9074 | 0.9333 | 0.9333 |
| TPR | 1.0000 | 0.9333 | 0.9333 | 0.9333 |
| FNR | 0.0000 | 0.0667 | 0.0667 | 0.0667 |
| FPR | 0.1111 | 0.1111 | 0.0556 | 0.0556 |
| precision | 0.7895 | 0.7778 | 0.8750 | 0.8750 |
| accuracy | 0.9216 | 0.9020 | 0.9412 | 0.9412 |
| specificity | 0.8889 | 0.8889 | 0.9444 | 0.9444 |
| F-Measure | 0.4412 | 0.4242 | 0.4516 | 0.4516 |

In summary, the results of the present invention suggest that, with the help of machine learning tools, using the established skin print features screening strategy (methods and steps), it is possible to construct an assisted screening system for Down syndrome based on only finger and palm print features (FIG. 6, Table 5) or based on only foot print features (Table 6). The assisted screening system for Down syndrome can also achieve an accuracy of more than 90% and a missed diagnosis rate of less than 10%.

In addition, after comparison, the present invention has proposed a better scheme that combines both foot prints and hand prints. The skin print screening system constructed by combining foot prints and hand prints can use fewer feature variables (6 feature items, namely V7-pattern on the ball of right foot; V33-left hand atd angle; V56-D5R inter-finger fold; V19-D4L the number of crest line; V29-left-hand print in IV zone; V23—whether left hand has an simian crease), achieves higher accuracy (>98%), detection rate (>93%), and the rate of missed diagnosis (<7%) and false positive rate (0%) were well controlled, so that it is more suitable for popularization and application (Table 2, FIG. 3).

Discussion

The American scientist Cummins (1976) first observed Down syndrome (also known as 21-trisomy syndrome, congenital stupidity, Down syndrome) patients with abnormal skin texture in 1936.

The skin prints have maintained their original basic crest line detail characteristics for a period from the formation of embryo to the death of the individual. Human skin prints are stable for his whole life and have long-term stability (or permanence), which mainly refers to that the geometric shape structure, angle, and arrangement of crest details etc. of each persons palm surface print are expanded and contracted with relative stability and simultaneously with the growth of fingers from childhood to adulthood of a person. Except that the thickness of the crest line and the area of the print may change with from childhood to adulthood, the details of the trend of the crest line will not change with age. After years of experimentation and research, British scholars have not only confirmed that fingerprints will be repeated, but also found that the fingerprints of the same person have not changed after 32 years (Herschel, W J (1916). The origin of finger-printing (H. Milford, Oxford University Press); Yager, N., and Amin, A. (2004). Fingerprint classification: a review. Pattern Analysis and Applications 7, 77-93). The stability of the pattern is also reflected in its tenacious recovery, as long as it does not damage the dermis so as to destroy the regeneration ability of the dermal nipple, even if the epidermis has a large area of shedding, it can gradually recover and remain unchanged (Galton, 1892).

Prior to the present invention, although many skin print workers have made efforts to use skin print features for disease screening. However, such studies of the mid-century were not satisfied due to complex operations (Walker, 1957; Beckman, 1965), low accuracy (Walker, 1957, Reed, 1970), and small number of samples (Otto, 1989; Bolling, 1971; Deckers, 1973). Further, all these previous studies had a problem of using the same data in model construction and evaluation, so it is difficult to achieve a satisfied and especially accurate early screening, so clinical promotion and application have not been achieved.

The inventors used the most comprehensive 56 skin print features (see Table A for definitions) of 256 patients with Down syndrome (41 cases from Hong Kong, China, 107 cases from Taiwan, 108 cases from Shanghai) and 800 normal control individuals (400 controls in Taizhou, 400 controls in Shanghai) to construct a screening system for Down syndrome with the help of specific machine learning methods. After strict screening of skin print features, a simple, accurate and efficient early screening system was constructed.

The inventors not only used the XGBoost machine learning algorithm (Chen, 2015; 2016) to build an assisted screening system for Down syndrome skin print, but also further adopted a support vector machine (SVM, support vector machine) (Suykens and Vandewalle, 1999) and linear discriminant analysis (LDA, Linear Discriminant Analysis) (Mika et al., 1999) and other methods for multi-directional verification. The results have showed that (a) no matter whether it is XGBoost, LDA, or SVM method, when the six selected skin print features are used as input data, FNR and accuracy are close to convergence. Even if additional feature items are added, the effect will not be essentially improved. (b) The results of 10-fold cross-validation show that XGBoost is superior to the other two methods, namely XGBoost is more robust to the stability of data selection.

The detection results of the assisted skin print screening method and equipment of the present invention in double-blind people have further confirmed that the assisted skin print screening method of the present invention has the outstanding advantages of accuracy, high efficiency and early stage detection, and can provide strong assistance for early intervention on patients with Down syndrome after birth.

All documents mentioned in the present invention are cited as references in this application, just as each document is individually cited as a reference. In addition, it should be understood that, after reading the above teaching content of the present invention, those skilled in the art can make various changes or modifications to the present invention, and these equivalent forms also fall within the scope defined by the appended claims of the present application.

REFERENCES

Weijerman, M. E., And D E Winter, J. P. (2011). Clinical Practice The Care of Children With Down Syndrome for Patient and Family 169, 11.

Kazemi, M., Salehi, M., & Kheirollahi, M. (2016). Down Syndrome: Current Status, Challenges and Future Perspectives. International Journal of Molecular And Cellular Medicine, 5 (3), 125.

Hanson, M. J. (2003). TWENTY-FIVE YEARS AFTER EARLY Intervention: A Follow-Up of Children With Down Syndrome and Their Families Infants & Young Children 16, 354-365.

Holder, E. H., Robinson, L. O., And Laub, J. H. (2011). The FingerPrint Sourcebook (US Department. Of Justice, Office of Justice Programs, National Institute of Justice).

Cummins, H., And Midlo, C. (1976). Finger Prints, Palms, and Soles: An Introduction to Dermatoglyphics, VOL 778 (Research Publishing Company).

Walker, N. f. (1958). The Use of Dermal Configurations in The Diagnosis of Mongolism. Pediatric Clinics of North America 5, 531-543.

Beckman, L., Gustayson, K., And Norring, A. (1965). Dermal configurations in the diagnosis of the down syndrome: An Attempt At A Simplified Scoring Method. Human Heredity 15, 3-12.

Reed, T. E., Borgaonkar, D. S., Conneally, P. m., Yu, P.-L., And Christian, J. C. (1970). Dermatoglyphic Nomograph for the Diagnosis of Down syndrome. The Journal of PediaTrics 77, 1024-1032.

OTTO, P. A., Vieira Filho, J., & Marques, S. A. (1989). Comparative Analysis of Dermatoglyphic INDs Used for Diagnosis of Down syndrome. Rev. Bras. Genet, 12 (1), 145-59.

Bolling, D. R., Borgaonkar, D. S., Herr, H. M., AND Davis, M. (1971). Evaluation of Dermal Prints in Down syndrome By Predictive Discrimination. Clinical Genetics 2, 163-169.

Deckers, J., Oorthuys, A., And Doesburg, W. (1973). Dermatoglyphics in Down syndrome. III. Clinical Genetics 4, 381-387.

CHEN, T., AND GUESTRIN, C. (2016). Xgboost: A Scalable Tree Boosting System. Paper Presented At: Proceedings of the 22nd ACM Sigkdd International Conference On Knowledge Discovery and Data Mining (ACM).

Chen, T., HE, T., AND BENESTY, M. (2015). Xgboost: Extreme Gradient Boosting. R Package Version 04-2, 1-4.

SuyKens, J. A., And Vandewalle, J. (1999). Least Squares Support Vector Machine Classifiers. Neral Processing Letters 9, 293-300.

Mika, S., Ratsch, G., Weston, J., Scholkopf, B., And Mullers, K.-R. (1999). Fisher Discriminant Analysis with kernels. Paper Presented At: Neural Networks for Signal Processing IX, 1999 Proceedings of The 1999 IEEE Signal Processing Society Workshop (IEEE).

What is claimed is:

1. An early assisted screening system for Down syndrome, which comprises:
   (a) a skin print feature input module, which is configured to input skin print features of a subject; wherein the skin print features comprise V7—pattern on the ball of right foot, V33—left hand atd angle, and V56—right hand D5R inter-finger fold(s);
   (b) a processing module for diagnosis of Down syndrome based on skin print, wherein the processing module performs a scoring processing on the inputted skin print features according to a predetermined evaluation criteria to obtain a risk score, and compares the risk score with a Down syndrome risk threshold, thereby obtaining an assisted screening result; wherein, when the risk score is higher than the risk threshold, it indicates that the subject's risk of Down syndrome is higher than that of a normal population; and when the risk score is lower than the risk threshold, it indicates that the subject's risk of Down syndrome is lower than that of the normal population; and
   (c) an output module for assisted screening result, which is configured to output the assisted screening result,
   wherein in the processing, a risk score processing is performed as follows:
   V7—pattern on the ball of right foot: when the arch print is present, the risk of disease increases;
   V33—left hand atd angle: when the angle is greater than 50 degrees, the risk of disease increases; and
   V56—D5R inter-finger fold: when there is only one inter-finger fold or the little finger is bent, the risk of disease increases.

2. The early assisted screening system for Down syndrome of claim 1, wherein the skin print features further comprise 1, 2, or 3 features selected from the following Group B:
   V 19—number of left-hand D4L crest line(s);
   V29—left-hand print in IV zone; and
   V23—whether left hand has a simian crease.

3. The early assisted screening system for Down syndrome of claim 2, wherein in the processing module, the risk score processing is further performed as follows:
   V19—D4L number of crest line: when the number of crest line is lower than an average of 11, the risk of disease increases;
   V29—Left hand print in IV zone: when the left-hand print in IV zone appears as a bow-shaped non-real print, the risk of disease increases; and
   V23—Whether left hand has a simian crease: when the left hand has a simian crease print, the risk of disease increases.

4. The early assisted screening system for Down syndrome of claim 1, wherein the skin print features comprise: V7—pattern on the ball of right foot; V33—left hand atd angle; V56—D5R inter-finger fold; V19—D4L number of crest line; V29—left V29—left hand print in IV zone; and V23—whether the left hand has a simian crease.

5. The early assisted screening system for Down syndrome of claim 1, wherein the skin print features further comprise at least 2 features selected from Group C1:
   V1, V54, V19, V16, V35, and V29;
   or, the skin print features further comprise at least one feature selected from Group C2:
   V55, V50, V28, V42, V44, and V43;
   and/or the skin print features further comprise at least one feature selected from Group D:
   V50, V28, V35, and V53.

6. The early assisted screening system for Down syndrome of claim 1, wherein the skin print features comprise the following six skin print features: V7, V33, V56, V19, V29, and V23, and optionally 1-4 skin print features selected from Group D consisting of V50, V28, V35, and V53.

7. The early assisted screening system for Down syndrome of claim 1, wherein the subject is an infant, a young people, or an adult.

8. The early assisted screening system for Down syndrome of claim 7, wherein the subject is 1 month to 44 years old, preferably 2 months to 10 years old, and more preferably 2 months to 5 years old.

9. The early assisted screening system for Down syndrome of claim 1, wherein the skin print feature input module is selected from the group consisting of: a skin print collector, a scanner, a keyboard, a tablet computer (PAD), a smartphone, and combinations thereof.

10. The early assisted screening system for Down syndrome of claim 1, wherein the processing module for diagnosis of Down syndrome based on skin print comprises a processor, and a memory in which the data of risk threshold of Down syndrome based on skin print feature are stored;
and/or the output module comprises a display, a printer, a tablet computer (PAD), or a smartphone.

11. A method for early assisted screening of Down syndrome, which comprises:
  (a) providing skin print features from a certain subject; wherein the skin print features comprise: V7—pattern on the ball of right foot, V33—left hand atd angle, and V56—right hand D5R inter-finger fold(s);
  (b) performing a diagnosis of Down syndrome based on skin print, wherein the performing comprises: implementing a scoring processing on the inputted skin print features according to a predetermined evaluation criteria to obtain a risk score, and comparing the risk score with a Down syndrome risk threshold, thereby obtaining an assisted screening result; wherein, when the risk score is higher than the risk threshold, it indicates that the subject's risk of Down syndrome is higher than that of a normal population; and when the risk score is lower than the risk threshold, it indicates that the subject's risk of Down syndrome is lower than that of the normal population,
wherein in the processing, a risk score processing is performed as follows:
  V7—pattern on the ball of right foot: when the arch print is present, the risk of disease increases;
  V33—left hand atd angle: when the angle is greater than 50 degrees, the risk of disease increases; and
  V56—D5R inter-finger fold: when there is only one inter-finger fold or the little finger is bent, the risk of disease increases.

12. The method of claim 11, wherein the skin print features comprise: V7—pattern on the ball of right foot; V33—left hand atd angle; V56—D5R inter-finger fold; V19—D4L number of crest line; V29—left hand print in IV zone; and V23—whether left hand has a simian crease.

* * * * *